United States Patent
Joseph

(10) Patent No.: US 11,860,174 B2
(45) Date of Patent: Jan. 2, 2024

(54) ANTI-CANNABIDIOL ANTIBODY AND USES THEREOF

(71) Applicant: BOMI, LLC, Reno, NV (US)

(72) Inventor: Bomi Joseph, Reno, NV (US)

(73) Assignee: BOMI LLC, Sparks, NV (US)

( * ) Notice: Subject to any disclaimer, the term of this patent is extended or adjusted under 35 U.S.C. 154(b) by 495 days.

(21) Appl. No.: 16/772,167

(22) PCT Filed: Dec. 14, 2018

(86) PCT No.: PCT/US2018/065658
§ 371 (c)(1),
(2) Date: Jun. 12, 2020

(87) PCT Pub. No.: WO2019/118831
PCT Pub. Date: Jun. 20, 2019

(65) Prior Publication Data
US 2021/0072265 A1 Mar. 11, 2021

Related U.S. Application Data

(60) Provisional application No. 62/599,501, filed on Dec. 15, 2017.

(51) Int. Cl.
*G01N 33/94* (2006.01)
*C07K 16/16* (2006.01)

(52) U.S. Cl.
CPC .......... *G01N 33/948* (2013.01); *C07K 16/16* (2013.01); *C07K 2317/622* (2013.01)

(58) Field of Classification Search
CPC .. C07K 16/16; C07K 16/44; C07K 2317/622; G01N 33/948
See application file for complete search history.

(56) References Cited

U.S. PATENT DOCUMENTS

2006/0019260 A1 1/2006 Lerner et al.
2009/0297449 A1 12/2009 Devy
2011/0086364 A1 4/2011 Takkinen et al.

FOREIGN PATENT DOCUMENTS

CN 101580544 B 10/2012

OTHER PUBLICATIONS

Search Opinion dated Nov. 29, 2021 for EP 3724657, Application No. 18887995.1, filed Dec. 14, 2018.*
International Search Report and Written Opinion for PCT/US2018/065658, dated May 6, 2019.
UniProtKB Accession No. P01649 for KV5AG-Mouse (1986).

* cited by examiner

*Primary Examiner* — Galina M. Yakovleva
(74) *Attorney, Agent, or Firm* — Banner & Witcoff, Ltd.

(57) ABSTRACT

This invention relates to anti-cannabidiol antibodies and methods of using these antibodies for the detection and quantification of bioactive cannabidiol.

17 Claims, 5 Drawing Sheets
Specification includes a Sequence Listing.

```
                           SEQUENCE LISTING

<160> NUMBER OF SEQ ID NOS: 10

<210> SEQ ID NO 1
<211> LENGTH: 6
<212> TYPE: PRT
<213> ORGANISM: Artificial
<220> FEATURE:
<223> OTHER INFORMATION: H-CDR1

<400> SEQUENCE: 1

Asn Phe Tyr Glu Met Trp
1               5

<210> SEQ ID NO 2
<211> LENGTH: 15
<212> TYPE: PRT
<213> ORGANISM: Artificial
<220> FEATURE:
<223> OTHER INFORMATION: H-CDR2

<400> SEQUENCE: 2

Ser Arg Asn Lys Ala Glu Asp Tyr Thr Thr Glu Tyr Ser Ala Ser
1               5                   10                  15

<210> SEQ ID NO 3
<211> LENGTH: 8
<212> TYPE: PRT
<213> ORGANISM: Artificial
<220> FEATURE:
<223> OTHER INFORMATION: H-CDR3

<400> SEQUENCE: 3

Ile Tyr Tyr Cys Ala Arg Asp Lys
1               5

<210> SEQ ID NO 4
<211> LENGTH: 7
<212> TYPE: PRT
<213> ORGANISM: Artificial
<220> FEATURE:
<223> OTHER INFORMATION: L-CDR1

<400> SEQUENCE: 4

Asp Leu Ser Gln Tyr Leu Phe
1               5

<210> SEQ ID NO 5
<211> LENGTH: 7
<212> TYPE: PRT
<213> ORGANISM: Artificial
<220> FEATURE:
<223> OTHER INFORMATION: L-CDR2

<400> SEQUENCE: 5

Arg Val Ser Arg Leu Thr His
1               5

<210> SEQ ID NO 6
<211> LENGTH: 9
<212> TYPE: PRT
<213> ORGANISM: Artificial
```

```
<220> FEATURE:
<223> OTHER INFORMATION: L-CDR3

<400> SEQUENCE: 6

Gln Gln Ser Arg Leu Ile Pro Asn Thr
1               5

<210> SEQ ID NO 7
<211> LENGTH: 123
<212> TYPE: PRT
<213> ORGANISM: Artificial
<220> FEATURE:
<223> OTHER INFORMATION: Heavy chain variable region

<400> SEQUENCE: 7

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asn Phe
            20                  25                  30

Tyr Glu Met Trp Val Arg Gln Ser Pro Gly Lys Arg Leu Glu Trp Ile
        35                  40                  45

Ala Ala Ser Arg Asn Lys Ala Glu Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
                85                  90                  95

Tyr Cys Ala Arg Asp Lys Asp Tyr Gly Ser Ser Tyr Trp Tyr Phe Asp
            100                 105                 110

Val Trp Gly Ala Gly Thr Thr Val Thr Val Ser
        115                 120

<210> SEQ ID NO 8
<211> LENGTH: 108
<212> TYPE: PRT
<213> ORGANISM: Artificial
<220> FEATURE:
<223> OTHER INFORMATION: Light chain variable region

<400> SEQUENCE: 8

Asp Ile Gln Asn Thr Gln Thr Pro Ser Ser Leu Ser Ala Ser Leu Gly
1               5                   10                  15

Asp Arg Val Ser Ile Ser Cys Arg Ala Ser Gln Asp Leu Ser Gln Tyr
            20                  25                  30

Leu Phe Trp Tyr Gln Gln Lys Pro Gly Gln Pro Lys Leu Leu Ile
        35                  40                  45

Tyr Arg Val Ser Arg Leu Thr His Gly Val Pro Asp Arg Phe Ser Gly
    50                  55                  60

Ser Gly Ser Gly Thr Asp Phe Thr Leu Thr Ile Asp Pro Asn Glu Glu
65                  70                  75                  80

Asp Asp Thr Ala Thr Tyr Phe Cys Gln Gln Ser Arg Leu Ile Pro Asn
                85                  90                  95

Thr Phe Gly Gly Gly Thr Lys Leu Glu Ile Lys Arg
            100                 105

<210> SEQ ID NO 9
<211> LENGTH: 432
<212> TYPE: PRT
<213> ORGANISM: Artificial
<220> FEATURE:
```

<223> OTHER INFORMATION: Heavy chain

<400> SEQUENCE: 9

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asn Phe
            20                  25                  30

Tyr Glu Met Trp Val Arg Gln Ser Pro Gly Lys Arg Leu Glu Trp Ile
        35                  40                  45

Ala Ala Ser Arg Asn Lys Ala Glu Asp Tyr Thr Thr Glu Tyr Ser Ala
    50                  55                  60

Ser Val Lys Gly Arg Phe Ile Val Ser Arg Asp Thr Ser Gln Ser Ile
65                  70                  75                  80

Leu Tyr Leu Gln Met Asn Ala Leu Arg Ala Glu Asp Thr Ala Ile Tyr
            85                  90                  95

Tyr Cys Ala Arg Asp Lys Asp Tyr Gly Ser Ser Tyr Trp Tyr Phe Asp
        100                 105                 110

Val Trp Gly Ala Gly Thr Thr Val Thr Val Ser Ser Glu Ser Ala Arg
    115                 120                 125

Asn Pro Thr Ile Tyr Pro Leu Thr Leu Pro Pro Ala Leu Cys Ser Asp
130                 135                 140

Pro Val Ile Ile Gly Cys Leu Ile His Asn Tyr Phe Pro Ser Gly Thr
145                 150                 155                 160

Met Asn Val Thr Trp Gly Lys Ser Gly Lys Asp Ile Thr Thr Val Asn
                165                 170                 175

Phe Pro Pro Ala Leu Ala Ser Gly Gly Arg Tyr Thr Met Ser Ser Gln
            180                 185                 190

Leu Thr Leu Pro Ala Val Glu Cys Pro Glu Gly Glu Ser Val Lys Cys
        195                 200                 205

Ser Val Gln His Asp Ser Asn Pro Val Gln Glu Cys Asp Val Asn Cys
    210                 215                 220

Ser Gly Pro Thr Pro Pro Pro Ile Thr Ile Gly Ser Cys Gln Pro
225                 230                 235                 240

Ser Leu Ser Leu Gln Arg Pro Ala Leu Glu Asp Leu Leu Leu Gly Ser
            245                 250                 255

Asp Ala Gln Ile Thr Cys Thr Leu Asp Gly Leu Arg Asn Pro Glu Gly
        260                 265                 270

Ala Val Phe Thr Trp Glu Pro Ser Thr Gly Lys Asp Ala Val Gln Lys
    275                 280                 285

Lys Ala Val Gln Asn Ser Cys Gly Cys Tyr Ser Val Ser Ser Val Leu
290                 295                 300

Pro Gly Cys Ala Glu Arg Trp Asn Ser Gly Ala Ser Phe Lys Cys Thr
305                 310                 315                 320

Val Thr His Pro Glu Ser Gly Thr Leu Thr Gly Thr Ile Ala Lys Val
                325                 330                 335

Thr Val Asn Thr Phe Pro Pro Gln Val His Leu Leu Pro Pro Pro Ser
            340                 345                 350

Glu Glu Leu Ala Leu Asn Gly Leu Leu Ser Leu Thr Cys Leu Val Arg
        355                 360                 365

Ala Phe Asn Pro Lys Glu Val Leu Val Arg Val Ser Ala Glu Asp Trp
    370                 375                 380

Lys Gln Gly Asp Gly Tyr Ser Cys Met Val Gly His Glu Ala Leu Pro
385                 390                 395                 400

```
Met Asn Phe Thr Gln Lys Thr Ile Asp Arg Leu Ser Gly Lys Pro Thr
                405                 410                 415

Gln Val Asn Val Ser Val Ile Met Ser Glu Gly Asp Gly Ile Tyr Cys
            420                 425                 430

<210> SEQ ID NO 10
<211> LENGTH: 204
<212> TYPE: PRT
<213> ORGANISM: Artificial
<220> FEATURE:
<223> OTHER INFORMATION: Light chain

<400> SEQUENCE: 10

Asp Ile Gln Asn Thr Gln Thr Pro Ser Ser Leu Ser Ala Ser Leu Gly
1               5                   10                  15

Asp Arg Val Ser Ile Ser Cys Arg Ala Ser Gln Asp Leu Ser Gln Tyr
            20                  25                  30

Leu Phe Trp Tyr Gln Gln Lys Pro Gly Gln Pro Pro Lys Leu Leu Ile
        35                  40                  45

Tyr Arg Val Ser Arg Leu Thr His Gly Val Pro Asp Arg Phe Ser Gly
    50                  55                  60

Ser Gly Ser Gly Thr Asp Phe Thr Leu Thr Ile Asp Pro Asn Glu Glu
65                  70                  75                  80

Asp Asp Thr Ala Thr Tyr Phe Cys Gln Gln Ser Arg Leu Ile Pro Asn
                85                  90                  95

Thr Phe Gly Gly Gly Thr Lys Leu Glu Ile Lys Arg Cys Pro Glu Gly
            100                 105                 110

Glu Ser Val Lys Cys Ser Val Gln His Asp Ser Asn Pro Val Gln Glu
            115                 120                 125

Leu Asp Val Asn Cys Ser Gly Pro Thr Pro Pro Pro Ile Thr Ile
    130                 135                 140

Gly Ser Cys Gln Pro Ser Leu Ser Leu Gln Arg Pro Ala Leu Glu Asp
145                 150                 155                 160

Leu Leu Leu Gly Ser Asp Ala Gln Ile Thr Cys Thr Leu Asp Gly Leu
                165                 170                 175

Arg Asn Pro Glu Gly Ala Val Phe Thr Trp Glu Pro Ser Thr Gly Lys
            180                 185                 190

Asp Ala Val Gln Lys Lys Ala Val Gln Asn Ser Cys
            195                 200
```

ANTI-CANNABIDIOL ANTIBODY AND USES THEREOF

This application is a national stage application under 35 U.S.C. § 371 of PCT Application No. PCT/US2018/065658, filed Dec. 14, 2018, which claims the benefit of U.S. Provisional Patent Application Ser. No. 62/599,501, filed Dec. 15, 2017, which is hereby incorporated by reference in its entirety.

FIELD OF THE INVENTION

This invention relates to anti-cannabidiol antibodies and methods of using these antibodies for the detection and quantification of bioactive cannabidiol.

BACKGROUND OF THE INVENTION

Cannabidiol ("CBD"), having the chemical name 2-(6-isopropenyl-3-methyl-2-cyclohexen-1-yl)-5-pentyl-1,3-benzenediol, is a non-psychoactive plant cannabinoid that has been recently discovered to have more medicinal properties than tetrahydrocannabinol (THC). Concern about the dangers of abuse led to the banning of marijuana and its constituents for medicinal use in United States and many other countries in the 1930s and 1940s. It took decades until cannabinoids came to be considered again as compounds of therapeutic value. However, still today their use in the United States is highly restricted despite their potential therapeutic value across a broad range of conditions including, e.g., arthritis, diabetes, alcoholism, multiple sclerosis, chronic pain, schizophrenia, post-traumatic distress syndrome, depression, infections, epilepsy, and other neurological disorders. In addition, several groups are actively investigating the anti-cancer properties of cannabidiol.

There are seven double bond isomers of 2-(6-isopropenyl-3-methyl-2-cyclohexen-1-yl)-5-pentyl-1,3-benzenediol. Only one of these isomers, i.e., the "Δ2-isomer", occurs in nature, while the other six isomers are formed when synthetic CBD is manufactured or when the natural isoform denatures. Cannabidiol is a ligand for the cannabinoid receptor type 2 (CB2), and its binding to this receptor mediates many of its therapeutic properties. Different isoforms of CBD bind to the CB2 receptor with different affinities, exerting varying levels of activity. Critical to the use of any CBD containing therapeutic, is knowledge of its bioactivity, i.e., the binding affinity of the CBD molecule to its cognate CB2 receptor. To date, agents and methods suitable for accurately quantifying the bioactivity of CBD do not exist. The present invention is directed at overcoming this and other deficiencies in the art.

SUMMARY OF THE INVENTION

A first aspect of the present disclosure is directed to an isolated antibody or antigen binding fragment thereof, wherein said antibody or antigen binding fragment there of binds to cannabidiol having the structure of Formula I

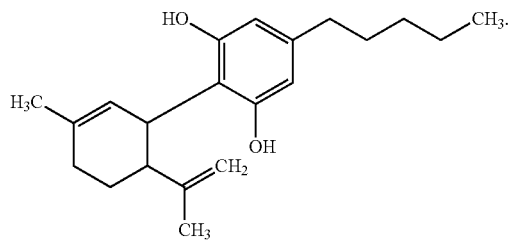

Formula I

Another aspect of the present invention is directed to a hybridoma producing the anti-cannabidiol antibody described herein.

Another aspect of the present invention is directed to an isolated polynucleotide encoding the anti-cannabidiol antibody described herein.

Another aspect of the present invention is directed to method of detecting cannabidiol in a sample. This method involves contacting the sample with the anti-CBD antibody or antigen binding fragment as described herein, and detecting the antibody or antigen binding fragment thereof bound to said cannabidiol if present in the sample.

Another aspect of the present invention is directed to a method of determining the bioactivity of cannabidiol. This method involves providing a sample containing a known amount of cannabidiol, and contacting the sample with the anti-CBD antibody or antigen binding fragment as described herein. The method further involves detecting the antibody or antigen binding fragment thereof bound to said cannabidiol in the sample; measuring the amount of detected antibody or antigen binding fragment thereof bound to said cannabidiol; and determining the bioactivity of the cannabidiol in the sample based on said measuring.

Another aspect of the present invention is directed to a kit that comprises the anti-cannabidiol antibody as described herein.

DETAILED DESCRIPTION OF THE INVENTION

Figure 1:
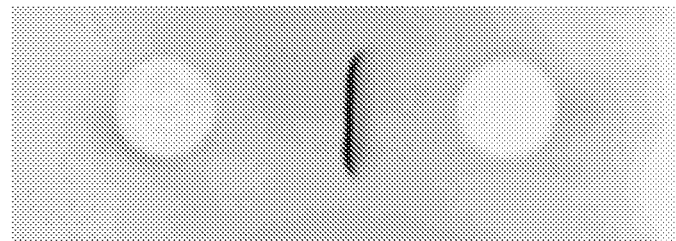
FIG. 1 depicts counter-immunoelectrophoresis of Cannabidiol-Antibody-Complex (CAC) in accordance with various embodiments of the present invention.

A first aspect of the present disclosure is directed to an isolated antibody or antigen binding fragment thereof, wherein said antibody or antigen binding fragment there of binds to cannabidiol (IUPAC name 2-[(1R,6R)-3-methyl-6-prop-1-en-2-ylcyclohex-2-en-1-yl]-5-pentylbenzene-1,3-diol) having the structure of Formula I

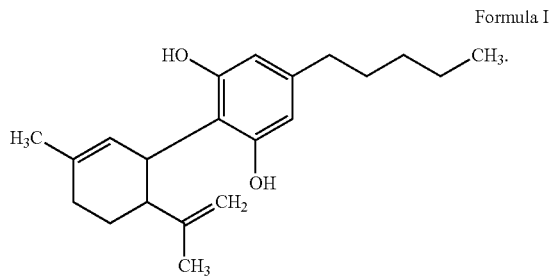 [SMILES: C=C(C)C1CCC(C)=CC1c1c(O)cc(CCCCC)cc1O]

Formula I

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired binding activity, i.e., binding cannabidiol.

An "isolated" antibody as used herein refers to an antibody which has been identified, separated and/or recovered from a component of its natural environment. For example, a composition comprising an antibody as described herein will be isolated and purified from a cell culture or other synthetic environment to greater than 60%, 70%, 80%, 85%, 90%, 95%, 96%, 97%, 98%, or 99% by weight of the antibody.

In one embodiment, the antibody of the disclosure is an immunoglobulin (Ig) molecule and comprises four polypeptide chains, i.e., two heavy (H) chains and two light (L) chains linked by disulfide bonds. Five types of mammalian Ig heavy chains are known: α, δ, ε, γ, and μ, wherein the type of heavy chain defines the class (isotype) of the antibody. Antibodies of the disclosure can be of any class (e.g., IgG, IgE, IgM, IgD, and IgA), and subclass (e.g., IgG1, IgG2, IgG3, IgG4, IgA1 and IgA2). The heavy chain may contain two regions, the constant region ($C_H$) and the variable region ($V_H$). The constant region shares high homology in all naturally occurring antibodies of the same isotype within the same species. Like the heavy chain, a light chain may also consist of one constant domain ($C_L$) and one variable domain ($V_L$). In mammals there are two types of immunoglobulin light chain, i.e., lambda (λ) and kappa (κ). The unique binding property or antigen binding specificity of a given antibody is determined by the variable (V) regions. In particular, three variable loops in each of the light ($V_L$) and the heavy ($V_H$) chain variable regions, known as complementarity determining regions (CDRs), are responsible for the antigen binding specificity. These regions of the antibody of the present invention are described in more detail infra.

An antibody fragment of the disclosure is a molecule containing an antigen binding region or antigen binding domain of a full antibody but is not the full antibody, e.g., the $V_H$ region, the $V_L$ region, or a combination of both regions. In one embodiment, the antibody fragment comprises a single-chain polypeptide containing one, two, or three of the CDRs of the light-chain variable domain. In another embodiment, the antibody fragment comprises a single-chain polypeptide containing one, two, or three of the CDRs of the heavy chain variable region. In another embodiment, the antibody fragment of the disclosure is a single domain antibody (also referred to as a nanobody), e.g., a peptide chain of about 110 amino acids long comprising one heavy chain variable region domain or one light chain variable region domain of a full antibody. In another embodiment, the antibody fragment is a fragment antigen-binding (F(ab)) fragment or a F(ab')$_2$ fragment.

Antibodies and antibody fragments of the present disclosure also encompass mutants, variants, or derivatives of the disclosed antibodies or fragments thereof which retain the essential epitope binding features of an Ig molecule. For example, the single domain antibodies can be derived from camelid ($V_H$H domains) or cartilaginous fish (V-NAR) variable domains, alone or fused to an Fc domain. In another embodiment, the antibody fragment comprises the heavy chain and light chain variable regions fused together to form a single-chain variable domain antibody (scFv) or a single-chain variable domain with an Fc portion (i.e., a scFv-Fc, e.g., a minibody.). In another embodiment, the antibody fragment is a divalent or bivalent single-chain variable fragment, engineered by linking two scFvs together either in tandem (i.e., tandem scFv), or such that they dimerize to form diabodies. In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$-$C_H$1-$V_H$-$C_H$1) that form a pair of antigen binding regions (see Zapata et al. *Protein Eng.* 8(10):1057-1062 (1995), which is hereby incorporated by reference in its entirety).

Antibody and antibody fragments disclosed herein can be mono-valent, bi-valent, or tri-valent with regard to binding domains, and the binding domains may be mono-specific, bi-specific, or tri-specific in binding specificity by design.

As noted above, the $V_H$ and $V_L$ regions of an antibody are subdivided into regions of hypervariability, termed complementarity determining regions (CDR). The CDRs are interspersed with regions that are more conserved in each family of V genes, termed framework regions (FR). These FR regions are specific to place in the proper spatial configuration the contact amino acid residues of the CDRs that are responsible for most of the binding capacity of the antibody. Each $V_H$ and $V_L$ is composed of three CDRs and four FRs, arranged from amino-terminus to carboxy-terminus in the following order: FR1, CDR1, FR2, CDR2, FR3, CDR3, FR4.

The three CDRs in each of the variable regions of the heavy chain and the light chain are designated CDR1, CDR2 and CDR3 for each of the variable regions (i.e., L-CDR1, L-CDR2 and L-CDR3 of the light chain variable region, and H-CDR1, H-CDR2, and H-CDR3 of the heavy chain variable region). The term "CDR set" refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991), which is hereby incorporated by reference in its entirety) not only provides an unambiguous residue numbering system applicable to any variable region of an antibody, but also provides precise residue boundaries defining the three CDRs.

In one embodiment, the antibody or binding fragment thereof described herein is a chimeric antibody. A chimeric antibody is an antibody where one portion of the amino acid sequence of each of the heavy and light chains is homologous to corresponding sequences in an antibody derived from a particular species or belonging to a particular class, while the remaining segment of each chain is homologous to corresponding sequences in another species or class. Typically the variable region of both light and heavy chains mimics the variable region of antibodies derived from one species of mammal, while the constant portions are homologous to sequences of antibodies derived from another. For example, the variable region can be derived from presently known sources using readily available B-cells or hybridomas from non-human host organisms in combination with constant regions derived from, for example, human cell preparations. Methods of making chimeric antibodies are well known in the art, see e.g., U.S. Pat. No. 4,816,567; and Morrison et al., "Chimeric human antibody molecules: mouse antigen-binding domains with human constant region domains"*Proc. Natl. Acad. Sci. USA* 81:6851-6855 (1984), which are hereby incorporated by reference in their entirety.

In another embodiment, the antibody or binding fragment thereof is a CDR-grafted antibody. A "CDR-grafted antibody" is an antibody which comprises heavy and light chain variable region sequences of one species, where one or more of the CDR regions are replaced with CDR regions of another species. For example, in one embodiment the CDR grafted antibody comprises human or humanized heavy and light chain variable regions, where one or more of the CDRs within these regions are replaced with one or more CDRs from another species, e.g., murine CDRs.

In another embodiment, the antibody or binding fragment thereof is a humanized antibody. A humanized antibody is an antibody or a variant, derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody comprises substantially all of at least one, and typically two, variable domains (Fab, Fab', F(ab')$_2$, Fv) in which all or substantially all of the CDR regions correspond to those of a non-human immunoglobulin (i.e., the donor antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," *Frontiers in Bioscience* 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones: Introduction to Gene Technology" (1987); Carter et al., *Proc. Natl. Acad. Sci. USA*, 89:4285 (1992); and Presta et al., *J. Immunol.*, 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain and light chain FR sequences known in the art can be used as heavy chain and light chain "acceptor" framework sequences (or simply, "acceptor" sequences) to humanize a non-human antibody using techniques known in the art (see e.g., Sims et al., *J. Immunol.*, 151:2296 (1993); Chothia et al., *J. Mol. Biol.*, 196:901 (1987), which are hereby incorporated by reference in their entirety). In one embodiment, human heavy chain and light chain acceptor sequences are selected from the framework sequences listed in publically available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the light chain as well as at least the variable domain of a heavy chain. The humanized antibody may further comprise the CH1, hinge, CH2, CH3, and CH4 regions of the heavy chain. In another embodiment, the humanized antibody comprises only a humanized light chain. In another embodiment, the humanized antibody comprises only a humanized heavy chain. In another embodiment, the humanized antibody comprises only a humanized variable domain of a light chain and/or a humanized variable domain of a heavy chain.

In one embodiment, the antibodies and binding fragments thereof as described herein are human antibodies. Methods of producing human antibodies that are known in the art are suitable for use in accordance with the present disclosure. For example, one can produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl Acad. Sci. USA* 90:2551 (1993); Jakobovits et al., *Nature* 362:255-258 (1993); U.S. Pat. No. 5,545,806 to Lonberg et al, U.S. Pat. No. 5,569,825 to Lonberg et al, and U.S. Pat. No. 5,545,807 to Surani et al, which are hereby incorporated by reference in their entirety.

The antibodies and binding fragments thereof described herein can be human antibodies or humanized antibodies (fully or partially humanized) as described supra. Alternatively, the antibodies and binding fragments thereof can be animal antibodies such as, but not limited to, a bird (for example, a duck or a goose), a shark, a whale, or a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.).

Methods of antibody production, in particular, monoclonal antibody production, may be carried out using the methods described herein and those well-known in the art (MONOCLONAL ANTIBODIES-PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest, i.e., 2-(6-isopropenyl-3-methyl-2-cyclohexen-1-yl)-5-pentyl-1,3-benzenediol, either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion,"*Eur J Immunol* 6:511 (1976), which is hereby incorporated by reference in its entirety). The immortal cell line, which may be murine or derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In accordance with the present invention, a hybridoma producing an anti-CBD antibody as described herein is referred to as the NAYAM BJ9003.236 hybridoma. Antibodies produced by this hybridoma comprise a variable heavy chain region having an amino acid sequence of SEQ ID NO: 7 as described in more detail herein, and a variable light chain region having an amino acid sequence of SEQ ID NO: 8, as described in more detail herein.

In another embodiment, monoclonal antibodies can be isolated from antibody phage libraries generated using the techniques described in McCafferty et al., "Phage Antibodies: Filamentous Phage Displaying Antibody Variable Domains,"*Nature* 348:552-554 (1990), which is hereby incorporated by reference in its entirety. Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., *BioTechnology* 10:779-783 (1992), which is hereby incorporated by reference in its entirety), as well as combinatorial infection and in vivo recombination as a strategy for constructing very large phage libraries (Waterhouse et al., *Nuc. Acids. Res.* 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In one embodiment, the anti-cannabidiol antibody or binding fragment thereof as described herein comprises a heavy chain variable region. The heavy chain variable region comprises a complementarity-determining region 1 (H-CDR1) comprising an amino acid sequence of SEQ ID NO: 1 (Asn-Phe-Tyr-Glu-Met-Trp), or a modified amino acid sequence of SEQ ID NO: 1, said modified sequence containing 1 or 2 amino acid residue modifications as compared to SEQ ID NO: 1. The heavy chain variable region further comprises a complementarity-determining region 2 (H-CDR2) comprising an amino acid sequence of SEQ ID NO: 2 (Ser-Arg-Asn-Lys-Ala-Glu-Asp-Tyr-Thr-Thr-Glu-Tyr-Ser-Ala-Ser), or a modified amino acid sequence of SEQ ID NO: 2, said modified sequence containing 1, 2, 3, or 4 amino acid residue modifications as compared to SEQ ID NO: 2. The heavy chain variable region further comprises a complementarity-determining region 3 (H-CDR3) comprising an amino acid sequence of SEQ ID NO: 3 (Ile-Tyr-Tyr-Cys-Ala-Arg-Asp-Lys), or a modified amino acid sequence of SEQ ID NO: 3, said modified sequence containing 1, 2, or 3 amino acid residue modifications as compared to SEQ ID NO: 3.

The antibody or binding fragment thereof as described herein may alternatively or further comprise a light chain variable region. The light chain variable region comprises a complementarity-determining region 1 (L-CDR1) having an amino acid sequence of SEQ ID NO: 4 (Asp-Leu-Ser-Gln-Tyr-Leu-Phe), or a modified amino acid sequence of SEQ ID NO: 4, said modified sequence containing 1 or 2 amino acid residue modifications as compared to SEQ ID NO: 4. The light chain variable region further comprises a complementarity-determining region 2 (L-CDR2) having an amino acid sequence of SEQ ID NO: 5 (Arg-Val-Ser-Arg-Leu-Thr-His), or a modified amino acid sequence of SEQ ID NO: 5, said modified sequence containing 1 or 2 amino acid residue modifications as compared to SEQ ID NO: 5. The light chain variable region further comprises a complementarity-determining region 3 (L-CDR3) having an amino acid sequence of SEQ ID NO: 6 (Gln-Gln-Ser-Arg-Leu-Ile-Pro-Asn-Thr), or a modified amino acid sequence of SEQ ID NO: 6, said modified sequence containing 1, 2, or 3 amino acid residue modifications as compared to SEQ ID NO: 6.

Suitable amino acid modifications to the heavy chain CDR sequences and/or the light chain CDR sequences of the anti-CBD antibody disclosed herein include, for example, conservative substitutions or functionally equivalent amino acid residue substitutions that result in variant CDR sequences having similar or enhanced binding characteristics to those of the CDR sequences disclosed herein. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences and the light chain CDR sequences as disclosed herein. Non-conservative substitutions involve substituting one or more amino acid residues of the CDR with one or more amino acid residues from a different class of amino acids to improve or enhance the binding properties of CDR.

The amino acid sequences of the heavy chain variable region CDRs and/or the light chain variable region CDRs of the anti-CBD antibody described herein may further comprise one or more internal neutral amino acid insertions or deletions that do not alter CBD binding. In one embodiment, the H-CDR3 having an amino acid sequence of SEQ ID NO: 3, further contains one or more internal neutral amino acid insertions or deletions that do not alter CBD binding. In another embodiment, the L-CDR1, having an amino acid sequence of SEQ ID NO: 4 further contains one or more internal neutral amino acid insertions or deletions that do not alter CBD binding.

In one embodiment of the present disclosure, the anti-CBD antibody or binding fragment thereof comprises a heavy chain variable region with a H-CDR1 having the amino acid sequence of SEQ ID NO: 1; a H-CDR2 having the amino acid sequence of SEQ ID NO: 2; and a H-CDR3 having the amino acid sequence of SEQ ID NO: 3. An exemplary heavy chain variable region comprising the aforementioned CDR regions has the amino acid sequence of SEQ ID NO: 7 as shown below. The CDR regions of the variable heavy chain of SEQ ID NO: 7 are underlined and the flanking framework regions (i.e., FR1-FR4) are shown in bold.

(SEQ ID NO: 7)
Glu-Val-Lys-Leu-Val-Glu-Ser-Gly-Gly-Gly$^{10}$-Leu-

Val-Gln-Pro-Gly-Gly-Ser Leu-Arg-Leu$^{20}$-Ser-Cys-

Ala-Thr-Ser-Gly-Phe-Thr-Phe-Ser$^{30}$-<u>Asn-Phe-Tyr-</u>

<u>Glu-Met-Trp</u>-Val-Arg-Gln-Ser$^{40}$-Pro-Gly-Lys Arg-

Leu-Glu-Trp-Ile Ala-Ala$^{50}$ <u>Ser Arg-Asn-Lys-Ala-</u>

<u>Glu-Asp-Tyr-Thr-Thr$^{60}$- Glu-Tyr-Ser-Ala-Ser-</u> Val-

Lys-Gly- Arg-Phe$^{70}$-Ile-Val-Ser-Arg-Asp-Thr-Ser-

Gln-Ser-Ile$^{80}$-Leu-Tyr-Leu-Gln-Met-Asp -Ala-Leu-

Arg-Ala$^{90}$-Glu-Asp-Thr-Ala-<u>Ile-Tyr-Tyr-Cys-Ala-</u>

<u>Arg$^{100}$-Asp-Lys</u>-Asp-Tyr-Gly-Ser-Ser-Tyr-Trp-

Tyr$^{110}$-Phe-Asp-Val-Trp-Gly-Ala-Gly-Thr-Thr-

Val$^{120}$-Thr-Val-Ser

In one embodiment of the present disclosure, the anti-CBD antibody or binding fragment thereof comprises a light chain variable region with a L-CDR1 having the amino acid sequence of SEQ ID NO: 4; a L-CDR2 having the amino acid sequence of SEQ ID NO: 5; and a L-CDR3 having the amino acid sequence of SEQ ID NO: 6. An exemplary light chain variable region comprising the aforementioned CDR regions has the amino acid sequence of SEQ ID NO: 8 as shown below. The CDR regions of the variable light chain of SEQ ID NO: 8 are underlined and the framework regions (i.e., FR1-FR4) are shown in bold.

(SEQ ID NO: 8)
Asp-Ile-Gln-Asn-Thr-Gln-Thr-Pro-Ser-Ser$^{10}$-Leu-Ser-

Ala-Ser-Leu-Gly-Asp-Arg-Val-Ser$^{20}$-Ile-Ser-Cys-Arg-

Ala-Ser-Gln-<u>Asp-Leu-Ser$^{30}$-Gln-Tyr-Leu-Phe</u>-Trp-Tyr-

Gln-Gln-Lys-Pro$^{40}$-Gly-Gln-Pro-Pro-Lys-Leu-Leu-Ile-

Tyr-<u>Arg$^{50}$-Val-Ser-Arg-Leu-Thr-His</u>-Gly-Val-Pro-

Asp$^{60}$-Arg-Phe-Ser-Gly-Ser-Gly-Ser-Gly-Thr-Asp$^{70}$-

Phe-Thr-Leu-Thr-Ile-Asp-Pro-Asn-Glu-Glu$^{80}$-Asp-Asp-

Thr-Ala-Thr-Tyr-Phe-Cys-Gln-Gln$^{90}$-Ser-Arg-Leu-Ile-Pro-Asn-Thr-Phe-Gly-Gly$^{100}$-Gly-Thr-Lys-Leu-Glu-Ile-Lys-Arg-

In one embodiment, the anti-CBD antibody or binding fragment thereof as described herein comprises a heavy chain variable region having an amino acid sequence of SEQ ID NO: 7 and/or a light chain variable region having an amino acid sequence of SEQ ID NO:8.

In another embodiment, the antibody or binding fragment thereof comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 7, and/or a light chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 8.

In another embodiment, the antibody or binding fragment thereof comprises a heavy chain having an amino acid sequence of SEQ ID NO: 9 as shown below. The CDRs of SEQ ID NOs: 1, 2, and 3 are underlined.

(SEQ ID NO: 9)
Glu Val Lys Leu Val Glu Ser Gly Gly Gly$^{10}$ Leu Val Gln Pro Gly Gly-Ser Leu-Arg Leu$^{20}$-Ser-Cys-Ala Thr-Ser Gly-Phe-Thr Phe Ser$^{30}$-Asn-Phe-Tyr-Glu-Met-Trp-Val-Arg-Gln-Ser$^{40}$ Pro-Gly-Lys Arg-Leu-Glu-Trp-Ile Ala-Ala$^{50}$ Ser Arg-Asn-Lys-Ala Glu-Asp-Tyr-Thr-Thr$^{60}$-Glu-Tyr-Ser-Ala-Ser-Val-Lys-Gly-Arg-Phe$^{70}$-Ile-Val-Ser-Arg-Asp Thr-Ser Gln-Ser-Ile$^{80}$-Leu-Tyr-Leu-Gln-Met-Asn-Ala-Leu-Arg-Ala$^{90}$-Glu-Asp-Thr-Ala Ile-Tyr-Tyr-Cys-Ala-Arg$^{100}$-Asp-Lys-Asp-Tyr-Gly-Ser-Ser-Tyr-Trp-Tyr$^{110}$-Phe-Asp-Val-Trp-Gly-Ala-Gly-Thr-Thr-Val$^{120}$-Thr-Val-Ser-Ser-Glu-Ser-Ala-Arg-Asn-Pro$^{130}$-Thr-Ile-Tyr-Pro-Leu-Thr-Leu-Pro-Pro-Ala$^{140}$-Leu-Cys-Ser-Asp-Pro-Val-Ile-Ile Gly-Cys$^{150}$-Leu-Ile-His-Asn-Tyr-Phe-Pro-Ser-Gly-Thr$^{160}$-Met-Asn-Val-Thr-Trp-Gly-Lys-Ser-Gly-Lys$^{170}$-Asp-Ile-Thr-Thr-Val Asn-Phe-Pro-Pro-Ala$^{180}$-Leu-Ala-Ser-Gly-Gly-Arg-Tyr-Thr-Met-Ser$^{190}$-Ser-Gln-Leu-Thr-Leu-Pro-Ala-Val-Glu-Cys$^{200}$-Pro-Glu-Gly-Glu-Ser-Val-Lys-Cys-Ser-Val$^{210}$-Gln-His-Asp-Ser-Asn-Pro-Val-Gln-Glu-Cys$^{220}$-Asp-Val-Asn-Cys-Ser-Gly-Pro-Thr-Pro-Pro$^{230}$-Pro-Pro-Ile-Thr-Ile-Gly-Ser-Cys-Gln-Pro$^{240}$-Ser-Leu-Ser-Leu-Gln-Arg-Pro-Ala-Leu-Glu$^{250}$-Asp-Leu-Leu Leu-Gly-Ser-Asp-Ala-Gln-Ile$^{260}$-Thr-Cys-Thr-Leu-Asp-Gly-Leu-Arg-Asn-Pro$^{270}$-Glu-Gly-Ala-Val-Phe-Thr-Trp-Glu-Pro-Ser$^{280}$-Thr-Gly-Lys-Asp-Ala-Val-Gln-Lys-Lys-Ala$^{290}$-Val-Gln-Asn-Ser-Cys-Gly-Cys-Tyr-Ser-Val$^{300}$-Ser-Ser-Val-Leu-Pro-Gly-Cys-Ala-Glu-Arg$^{310}$-Trp-Asn-Ser-Gly-Ala-Ser-Phe-Lys-Cys-Thr$^{320}$-Val-Thr-His-Pro-Glu-Ser-Gly-Thr-Leu-Thr$^{330}$ Gly-Thr-Ile-Ala-Lys-Val-Thr-Val-Asn-Thr$^{340}$-Phe-Pro-Pro-Gln-Val-His-Leu-Leu-Pro-Pro$^{350}$-Pro-Ser-Glu-Glu-Leu-Ala-Leu-Asn-Gly-Leu$^{360}$-Leu-Ser-Leu-Thr-Cys-Leu-Val-Arg-Ala-Phe$^{370}$-Asn-Pro-Lys-Glu-Val-Leu-Val-Arg-Val-Ser$^{380}$-Ala-Glu-Asp-Trp-Lys-Gln-Gly-Asp-Gly-Tyr$^{390}$-Ser-Cys-Met-Val-Gly-His-Glu-Ala-Leu-Pro$^{400}$-Met-Asn-Phe-Thr-Gln-Lys-Thr-Ile-Asp-Arg$^{410}$-Leu-Ser-Gly-Lys-Pro-Thr-Gln-Val-Asn-Val$^{420}$-Ser, Val-Ile-Met-Ser-Glu-Gly-Asp-Gly-Ile$^{430}$-Tyr-Cys.

In another embodiment, the antibody or binding fragment thereof comprises a light chain having an amino acid sequence of SEQ ID NO: 10 as shown below. The light chain CDRs of SEQ ID NOs: 4, 5, and 6 are underlined.

(SEQ ID NO: 10)
Asp-Ile-Gln-Asn-Thr-Gln-Thr-Pro-Ser-Ser$^{10}$-Leu-Ser-Ala-Ser-Leu-Gly-Asp-Arg-Val-Ser$^{20}$-Ile- Ser-Cys-Arg-Ala-Ser-Gln-Asp-Leu-Ser$^{30}$ Gln-Tyr-Leu-Phe-Trp-Tyr-Gln-Gln-Lys-Pro$^{40}$-Gly-Gln-Pro Pro Lys Leu Leu Ile Tyr Arg$^{50}$ Val Ser Arg Leu Thr His Gly Val Pro Asp$^{60}$ Arg Phe Ser Gly Ser Gly Ser Gly Thr Asp$^{70}$ Phe Thr Leu Thr Ile Asp Pro Asn Glu Glu$^{80}$ Asp Asp Thr Ala Thr Tyr Phe Cys Gln Gln$^{90}$ Ser Arg Leu Ile Pro Asn Thr Phe Gly Gly$^{100}$ Gly Thr Lys Leu Glu Ile Lys Arg Cys-Pro$^{110}$-Glu-Gly-Glu-Ser-Val-Lys-Cys-Ser-Val-Gln$^{120}$-His-Asp-Ser-Asn-Pro-Val-Gln-Glu-Leu-Asp$^{130}$-Val-Asn-Cys-Ser-Gly-Pro-Thr-Pro-Pro-Pro$^{140}$-Pro-Ile-Thr-Ile-Gly-Ser-Cys-Gln-Pro-Ser$^{150}$-Leu-Ser-Leu-Gln-Arg-Pro-Ala-Leu-Glu-Asp$^{160}$-Leu-Leu Leu-Gly-Ser-Asp-Ala-Gln-Ile-Thr$^{170}$-Cys-Thr-Leu-Asp-Gly-Leu-Arg-Asn-Pro-Glu$^{180}$-Gly-Ala-Val-Phe-Thr-Trp-Glu-Pro-Ser-Thr$^{190}$-Gly-Lys-Asp-Ala-Val-Gln-Lys-Lys-Ala-Val$^{200}$-Gln-Asn-Ser-Cys

In one embodiment, the anti-CBD antibody or binding fragment thereof as described herein comprises a heavy chain having an amino acid sequence of SEQ ID NO: 9 and/or a light chain having an amino acid sequence of SEQ ID NO: 10.

In another embodiment, the antibody or binding fragment thereof comprises a heavy chain having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 9, and/or a light chain having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 10.

Figure 3:
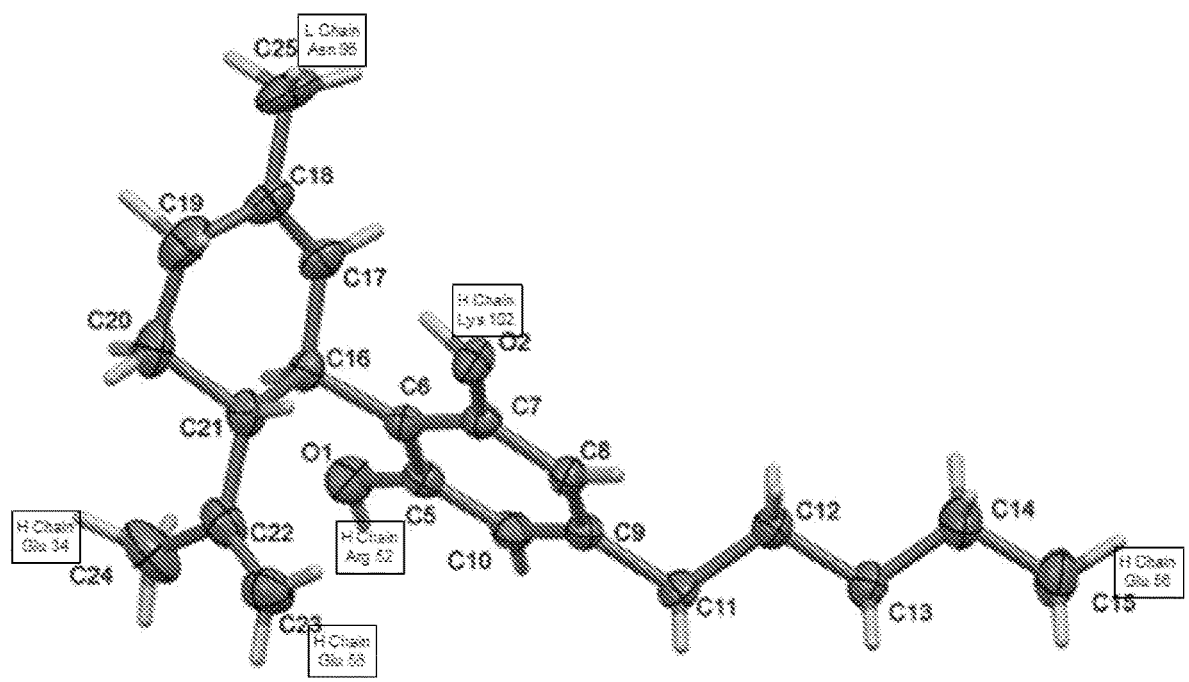
FIG. 3 shows the epitopic determinants of cannabidiol and the amino acid residues of the anti-CBD antibody critical for selective binding to those epitopic determinants.

Antibody "specificity" refers to selective recognition of the antibody or binding portion thereof as described herein for a particular epitope or epitopes of CBD. The term "epitope" includes any determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. FIG. 3 shows the epitopic determinants of CBD and identifies the amino acid residues within the CDR regions of the anti-CBD antibody that are critical for binding these epitopes of CBD. In particular, amino acid residue 34 (SEQ ID NO: 7) of the heavy chain CDR1, amino acid residues 52 and 56 (SEQ ID NO: 7) of the H-CDR2, amino acid residue 102 (SEQ ID NO: 7) of the H-CDR3, and amino acid residue 96 (SEQ ID NO: 8) of the light chain CDR3 are critical for antibody binding to CBD.

The antibody or antigen binding fragment thereof as described herein binds specifically to CBD. The antibody or binding fragment thereof as described herein binds with the highest affinity to the naturally occurring 2-(6-isopropenyl-3-methyl-2-cyclohexen-1-yl)-5-pentyl-1,3-benzenediol isoform of CBD. The antibody or binding fragment thereof as described herein also binds to other isoforms of CBD, albeit at lower affinity relative to its binding to the 42-isomer of CBD. "Binds specifically" as used herein refers to an antibody binding to its antigen and is not intended to exclude low-level, non-specific binding that may occur between random proteins. "Binds specifically" as used herein is not intended and does not imply that the antibody will not bind to any protein or molecule other than the molecule(s) as disclosed herein since antibodies can cross-react with any molecule or protein that includes the relevant epitope.

Another aspect of the present disclosure relates to an antibody or binding portion thereof that competes for binding to CBD with the anti-CBD antibody described herein, i.e., the antibody comprising a heavy chain variable region comprising an H-CDR1 of SEQ ID NO: 1, an H-CDR2 of SEQ ID NO: 2, and an H-CDR3 of SEQ ID NO: 3, and a light chain variable region comprising L-CDR1 of SEQ ID NO: 4, L-CDR2 of SEQ ID NO: 5, and L-CDR3 of SEQ ID NO: 6. In accordance with this aspect of the disclosure, the antibody or binding portion thereof competes for binding to the Δ-2 isomer of CBD.

In accordance with this aspect of the disclosure, a competitive binding assay, such as Bio-Layer Interferometry (BLI) can be utilized to identify an antibody or binding portion thereof that competes for binding to CBD with the anti-CBD antibody described in detail herein. Other competitive binding assays known in the art can also be utilized to identify a competitive binding antibody in accordance with this aspect of the disclosure.

Another aspect of the present disclosure is directed to one or more isolated polynucleotides encoding the antibody or binding fragment thereof as described herein. In one embodiment, the isolated polynucleotide encodes all or at least a portion of the heavy chain variable region having the amino acid sequence of SEQ ID NO: 7. In one embodiment, the isolated polynucleotide encodes all or at least a portion of the heavy chain having the amino acid sequence of SEQ ID NO: 9. In another embodiment, the isolated polynucleotide encodes all or at least a portion of the light chain variable region having the amino acid sequence of SEQ ID NO: 8. In another embodiment, the isolated polynucleotide encodes all or at least a portion of the light chain having the amino acid sequence of SEQ ID NO: 10. In another embodiment, the isolated polynucleotide encodes a combination of all or portions of SEQ ID NOs: 7, 8, 9, and 10.

The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the disclosure is directed to a vector comprising at least one polynucleotide as described herein. Such vectors may be plasmid vectors, viral vectors, vectors for baculovirus expression, transposon based vectors or any other vector suitable for introduction of the polynucleotides described herein into a given organism or genetic background by any means.

Another embodiment of the disclosure is directed to one or more expression vectors comprising the polynucleotides encoding the antibody or binding fragment thereof as described herein. The polynucleotide sequences encoding the heavy and light chain variable domains, Fab fragments, or full-length chains of the antibodies disclosed herein are combined with sequences of promoter, translation initiation, 3' untranslated region, polyadenylation, and transcription termination to form one or more expression vector constructs.

In accordance with this embodiment, the expression vector construct encoding the anti-CBD antibody or binding portion thereof can include the nucleic acid encoding the heavy chain polypeptide, a fragment thereof, a variant thereof, or combinations thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region. In some embodiments, the heavy chain polypeptide can include a VH region and a CH1 region. In other embodiments, the heavy chain polypeptide can include a VH region, a CH1 region, a hinge region, a CH2 region, and a CH3 region.

The expression construct can also include a nucleic acid sequence encoding the light chain polypeptide, a fragment thereof, a variant thereof, or combinations thereof. The light chain polypeptide can include a variable light chain (VL) region and/or a constant light chain (CL) region.

The expression construct also typically comprises a promoter sequence suitable for driving expression of the antibody or binding fragment thereof. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP) a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein.

The expression construct can further encode a linker sequence. The linker sequence can encode an amino acid sequence that spatially separates and/or links the one or more components of the expression construct (heavy chain and light chain components of the encoded antibody).

Another embodiment of the invention is a host cell comprising the polynucleotides and/or vectors described herein. The antibodies and binding fragments thereof described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

The host cell chosen for expression may be of mammalian, e.g., COS-1, COS-7, HEK293, BHK21, CHO, BSC-1, He G2, SP2/0, HeLa, myeloma, or lymphoma cell. The host cell can alternatively be a yeast cell, an insect cell, a plant cell, or any derivative, immortalized or transformed cell thereof. Alternatively, the host cell may be selected from a species or organism incapable of glycosylating polypeptides, e.g., a prokaryotic cell or organism, such as BL21, BL21(DE3), BL21-GOLD(DE3), XL1-Blue, JM109, HMS174, HMS174(DE3), and any of the natural or engineered E. coli spp., Klebsiella spp., or Pseudomonas spp. strains.

The antibodies described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium.

Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), which is hereby incorporated by reference in its entirety). Other suitable mammalian host cells include, without limitation, NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibody fragments, such as Fab fragments or scFv molecules. It is understood that variations on the above procedure are within the scope of the present disclosure. For example, it may be desirable to transfect a host cell with DNA encoding functional fragments of either the light chain and/or the heavy chain of an antibody described herein. Recombinant DNA technology may also be used to remove some or all of the DNA encoding either or both of the light and heavy chains that is not necessary for binding to the antigens of interest. The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification. Protease inhibitors may be used to inhibit proteolytic degradation during purification. One skilled in the art will appreciate that purification methods suitable for the antibody of interest may require modification to account for changes in the character of the antibody upon expression in cell culture.

Another aspect of the present invention is directed to method of detecting cannabidiol in a sample. This method involves contacting the sample with the antibody or antigen binding fragment that binds cannabidiol as described herein, and detecting the antibody or antigen binding fragment thereof bound to cannabidiol, i.e., the anti-CBD antibody-CBD complex, if present in the sample.

Methods described herein involving the detection of CBD in a sample involve the use of a detectably labeled anti-CBD antibody as described herein. Accordingly, in one aspect the anti-CBD antibody as described herein may be coupled to a detectable label. Suitable detectable labels are well known in the art and include detectable tags (e.g., a poly-histidine (His$_6$-) tag, a glutathione-S-transferase (GST-) tag, or a maltose-binding protein (MBP-) tag); radioactive labels (e.g., carbon ($^{14}$C) or phosphorous ($^{32}$P)); fluorescent labels (e.g., hydroxycoumarin, succinimidyl ester, aminocoumarin, methoxycoumarin, Cascade Blue™, Hydrazide, Pacific Blue™ Maleimide, Pacific Orange®, Lucifer yellow, NBD, NBD-X, R-Phycoerythrin (PE), a PE-Cy5™ conjugate (Cychrome, R670, Tri-Color, Quantum Red), a PE-Cy7™ conjugate, Red 613, PE-Texas Red®, PerCP, Peridinin chlorphyll protein, TruRed (PerCP-Cy5.5™ conjugate), FluorX, Fluoresceinisothyocyanate (FITC), BODIPY™-FL, TRITC, X-Rhodamine (XRITC), Lissamine™ Rhodamine B, Texas Red®, Allophycocyanin (APC), an APC-Cy7™ conjugate, Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, Alexa Fluor® 790, Cy2™, Cy3™, Cy3B™, Cy3.5™, Cy5™, Cy5.5™ or Cy7™); luminescent labels (e.g., luminol); bioluminescent labels (e.g., luciferase, luciferin, and aequorin); or enzymatic labels (e.g., luciferin, 2,3-dihydrophthalazinedi ones, malate dehydrogenase, urease, peroxidases (e.g., horseradish peroxidase), alkaline phosphatase, b-galactosidase, glucoamylase, lysozyme, saccharide oxidases (e.g., glucose oxidase, galactose oxidase, and glucose-6-phosphate dehydrogenase), heterocyclic oxidases (e.g., uricase and xanthine oxidase), lactoperoxidase, microperoxidase). Alternatively, the CBD-antibody can be bound by a detectable label, for example, bound by a secondary antibody that contains a detectable label.

Detection assays for detecting the anti-CBD antibody bound to a cannabidiol in a sample are well known in the art and include, for example, immunoprecipitation, enzyme-linked immunosorbent assay (ELISA), radioimmunoassay (RIA), or fluorescent activated cell sorting (FACS).

Another aspect of the present invention is directed to a method of determining the bioactivity of cannabidiol. This method involves providing a sample containing a known amount of cannabidiol, and contacting the sample with the antibody or antigen binding fragment that binds cannabidiol as described herein. The method further involves detecting the antibody or antigen binding fragment thereof bound to said cannabidiol in the sample; measuring the amount of detected antibody or antigen binding fragment thereof bound to said cannabidiol; and determining the bioactivity of the cannabidiol in the sample based on said measuring.

As discussed supra, CBD binds the CB2 receptor, and the bioactivity of CBD in any CBD containing sample (e.g., plant extract) is measured by the binding affinity of CBD for its receptor. The anti-CBD antibody of the present invention simulates the CB2 receptor, acting as a surrogate agent by which the binding affinity of CBD to its receptor can be measured in vitro. The antibody binds most strongly to the native, natural form of CBD (i.e., 2-(6-isopropenyl-3-methyl-2-cyclohexen-1-yl)-5-pentyl-1,3-benzenediol)). Solvent extraction, heating, high speed shear of the CBD molecule, the type of plant and the part of the plant from which the CBD is extracted, etc., all affect antibody-CBD binding. Thus, the bioactivity of CBD in any composition containing CBD can readily be determined by measuring the binding affinity between the anti-CBD antibody described herein and CBD in the composition, and comparing it to the binding affinity between the anti-CBD antibody and the natural isoform of CBD. Bioactivity of CBD in a sample is expressed as a percentage of maximal activity, i.e., the percentage of activity relative to the natural isoform of CBD.

Assays and methods for detecting anti-CBD antibody and CBD complexes, along with suitable detectable labels are described supra. Additional assays suitable for quantitatively assessing binding affinity include, without limitation, radioactive binding assays, non-radioactive binding assays (e.g., fluorescence resonance energy transfer assays or surface plasmon resonance), solid phase ligand binding assays, and liquid phase ligand binding assays (e.g., immunoprecipitation).

Another aspect of the present invention is directed to a kit that comprises the anti-cannabidiol antibody as described herein. In one embodiment, the kit is an assemblage of materials or components, including at least one of the inventive antibodies or antigen binding fragments as described herein that is useful for measuring the bioactivity of CBD in a sample.

The exact nature of the components configured in the inventive kit depends on its intended purpose. Instructions for use may be included in the kit. "Instructions for use" typically include a tangible expression describing the technique to be employed in using the components of the kit to effect a desired outcome, such as to test for bioactive CBD or to quantify the amount of CBD. Optionally, the kit also contains other useful components, such as, substrates, syringes, applicators, pipetting or measuring tools, or other useful reagents as will be readily recognized by those of skill in the art.

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays. As used herein, the term "package" refers to a suitable solid matrix or material such as glass, plastic, paper, foil, and the like, capable of holding the individual kit components. Thus, for example, a package can be a glass vial used to contain suitable quantities of a purified antibody that binds specifically to CBD as described herein. The packaging material generally has an external label which indicates the contents and/or purpose of the kit and/or its components.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be

EXAMPLES

Examples are provided below to illustrate the present invention. These examples are not meant to constrain the present invention to any particular application or theory of operation

Example 1

Production of the Anti-Cannabidiol Antibody

Cannabidiol (2-[(1R,6R)-6-isopropenyl-3-methylcyclohex-2-en-1-yl]-5-pentylbenzene-1,3-diol) was obtained from 1) Hebrew University of Jerusalem, Rehovot, Israel, and 2) ImmunAG, LP, Goa, India.

Step 1—5% Cannabidiol was dissolved in Caproic acid (C5H11COOH) and this solution was injected into BALB/Lac mice. 0.2 ml were intravenously injected into the lateral tail vein with a 27-28 mm gage needle. The injections were repeated every other day for 14 days, for a total of 7 injections.

Step 2—Each injection was followed by an in vivo electroporation, which significantly enhanced the immune response. This was done by sending 80 pulses of 100 microseconds at 0.3 Hz with an electrical field magnitude of 2500 V/cm.

Step 3—Spleen cells of the mice immunized with Cannabidiol were isolated. Monoclonal antibodies were made by cell culture that involved fusing myeloma cells with the spleen cells immunized with Cannabidiol-creating a fused "Splenocyte". The fusion of the B cells with myeloma cells was done by electrofusion. The BTX ECM 2001 Electrofusion generator cell fusion applications manufactured by BTX Harvard Apparatus, Holliston Mass. USA were used for the fusion. The two cells were fused by dielectrophoresis which used a high frequency alternating current. Once the cells were brought together, a pulsed voltage was applied. The pulsed voltage caused the cell membrane to permeate and subsequently the membranes of the two cells to combine and fuse. After this, an alternative voltage was applied again for a brief period of time to stabilize the process. The end result was that the mixed cytoplasm and the cell membranes were completely fused. The two nuclei fused later within the cell making the resulting "heterokaryon" cell.

Step 4—The fused cells were incubated in HAT (hypoxanthine-aminopterin-thymidine) medium for roughly 10 to 14 days. The aminopterin blocked the pathway for nucleotide synthesis and killed any unfused myeloma cells. Only the B cell-myeloma hybrids survive. These cells produced antibodies (a property of B cells) and are immortal (a property of the myeloma cells). The incubated medium was then diluted into multi-well plates to such an extent that each well only contained one cell.

Step 5—The next stage was a rapid primary screening technique, ELISA, to identify and select only those hybridomas that produce antibodies of appropriate specificity. Solid-phase enzyme immunoassay (EIA) was used to detect the presence of Cannabidiol in liquid samples. The Cannabidiol from the sample were attached to the surface. Then the antibody produced in the incubated medium was applied over the surface so it could bind to the Cannabidiol.

This antibody was linked to a Cytochrome P450 enzyme (CYP1A1, CYP1A2, CYP2C9, CYP2C19, CYP2D6, CYP3A4, and CYP3A5 all worked) and the final step was the addition of a substance containing Cytochrome P450 substrate (such as Pentalenolactone). The subsequent reaction produced a detectable color change in the substrate.

Step 6—The B cells that produced the desired antibodies were cloned to produce numerous identical daughter clones. Supplemental media cultures containing interleukin-6 were used to establish a hybridoma colony. They grew well in culture medium RPMI-1640 (with antibiotics and fetal bovine serum) and produced numerous antibodies. The smaller multi-well plates used to grow the hybridomas, were changed to larger tissue culture flasks. The culture supernatant yielded 46 µg/ml to 72 µg/ml of Cannabidiol monoclonal antibody, which was maintained at −20° C. or lower until used.

Example 2

Analyzing the Bioactivity of CBD by Immunoelectrophoresis

Immunoelectrophoresis was used test the Cannabidiol-Antibody-Complex ("CAC"). There are several variants to this procedure, all of which require CAC.

Agarose as 1% gel slabs of about 1 mm thickness, buffered at high pH (around 8.6) is a preferred medium. An electrophoresis equipment with a horizontal cooling plate appear to works best.

FIG. 1 is a separation and identification of CAC using Counter-immunoelectrophoresis. This is similar to immunodiffusion, but with the addition of an electrical field across the agarose medium. There is more rapid migration of the Cannabidiol and antigen out of their respective wells towards one another to form a line of precipitation, indicating binding

Example 3

Analyzing the Bioactivity of CBD by Immunofluorescence

Figures 2A, 2B, 2C, 2D, 2E:
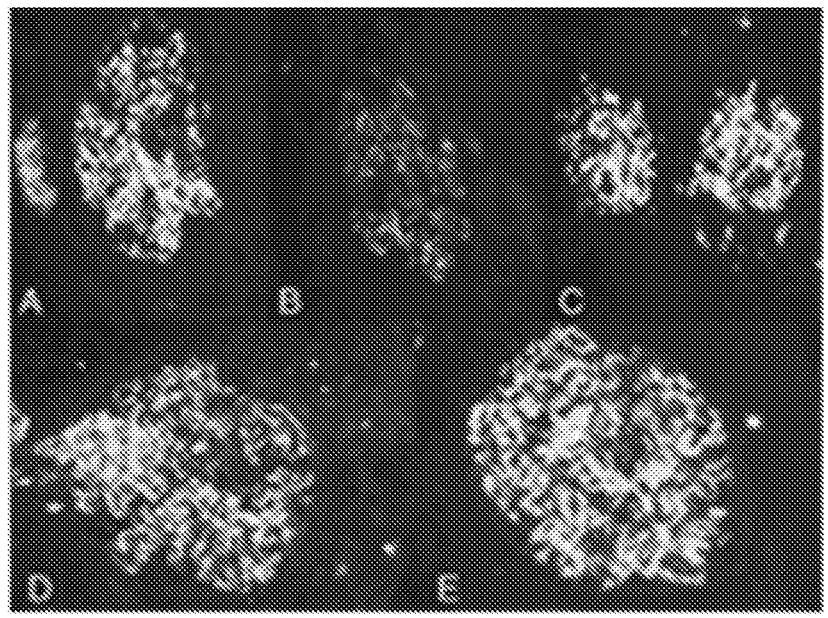
FIGS. 2A-2E show the quantitative assessment of cannabidiol bioactivity using the anti-cannabidiol antibody of the invention. The anti-cannabidiol antibody is coupled to fluorescein, and quantitation of the fluorescein intensity is used to calculate the percentage of maximal activity exhibited by the cannabidiol in the sample. Maximal activity is the activity exhibited by a pure sample of the Δ2-isomer of cannabidiol. The sample of FIG. 2A exhibits 38% maximal activity, the sample of FIG. 2B exhibits 18% of maximal activity, the sample of FIG. 2C exhibits 63% of maximal activity, the sample of FIG. 2D exhibits 52% maximal activity, and the sample of FIG. 2E exhibits 76% of maximal activity.

For this experiment, the anti-CBD antibody as described herein was labeled with the fluorescent molecule, fluorescein. FIG. 2 shows the fluorescein labeled anti-CBD antibody bound to CBD in various CBD containing samples. The bioactivity of CBD is quantified by measuring the intensity of the light emitted by the fluorescein label of the bound anti-CBD antibody and comparing it to the intensity of light emitted by fluorescein labeled anti-CBD antibody bound to the same amount of the Δ2-isomer of CBD.

Materials and Methods for Examples 4-7

CHO cells and membrane preparation. These were stably transfected with cDNA encoding human CB2 receptors. The $CB_2$-transfected cells were used in binding assays with [3H]-CP55940, [3H]-WIN55212-2 or [35S]-GTPγS (Bmax=72.5 pmol mg−1 protein). The clones used in the assays were the same as those used in the sPAP reporter assay described by Green et al. (1998). Cells were maintained at 37° C. and 5% $CO_2$ in DMEM (f-12 HAM) with 2 mm Glutamine, Geneticin (600 µg ml−1) and Hygromycin (300 µg ml−1). Because receptor over expression may lead to the activation of effector mechanisms to which receptors in natural membranes are not normally coupled (Kenakin, "Agonist-receptor Efficacy II: Agonist Trafficking of Receptor Signals," *Trends in Pharmacological Sciences* 16(7):

232-238 (1995), which is hereby incorporated by reference in its entirety)), the assays were performed with cells expressing fewer $CB_2$ receptors than the cells used in the binding assays. CHO cells were suspended in 50 mm Tris buffer (pH 7.4) and 0.32 m sucrose and homogenized with an Ultra-Turrex homogenizer. The homogenate was diluted with 50 mm Tris buffer (pH 7.4) and centrifuged at 50,000×g for 1 hour to isolate the membranes.

CHO—$CB_2$ binding. A filtration procedure was used to measure [3H]-CP55940 and [3H]-WIN55212-2 binding. This is a modification of the method described by Compton et al., "Cannabinoid Structure-activity Relationships: Correlation of Receptor Binding and In Vivo Activities," *Journal of Pharmacology and Experimental Therapeutics* 265(1): 218-226 (1993), which is hereby incorporated by reference in its entirety. Binding assays were performed with [3H]-CP55940 or [3]-WIN55212-2, 1 mm $MgCl_2$, 1 mm EDTA, 2 mg ml−1 bovine serum albumin (BSA) and 50 mm Tris buffer, total assay volume 500 µl. Binding was initiated by the addition of cell membranes (20-30 µg protein). Assays were carried out at 30° C. for 90 minutes before termination by addition of ice-cold wash buffer (50 mm Tris buffer, 1 mg ml−1 BSA) and vacuum filtration using a 12-well sampling manifold (Brandel Cell Harvester) and Whatman GF/B glass-fibre filters that had been soaked in wash buffer at 4° C. for 24 hours. Each reaction tube was washed three times with a 4 ml aliquot of buffer. The filters were oven-dried for 60 minutes and then placed in 5 ml of scintillation fluid (Ultima Gold XR, Packard). Radioactivity was quantified by liquid scintillation spectrometry. Specific binding was defined as the difference between the binding that occurred in the presence and absence of 1 µm reference cannabidiol. Protein assays were performed using a Bio-Rad Dc kit. Unlabeled and radio labelled cannabidiol were each added in a volume of 50 µl following dilution in assay buffer (50 mm Tris buffer containing 10 mg ml−1 BSA). The concentration of [3H]-CP55940 or [3H]-WIN55212-2 used in displacement assays was 0.5 nm. The concentrations of cannabidiol that produced a 50% displacement of radio ligand from specific binding sites (IC50 values) were calculated using GraphPad Prism (GraphPad Software, San Diego, U.S.A.). Competitive binding curves were fitted with minimum values for displacement of radio ligand from specific binding sites constrained to zero. Dissociation constant (Ki) values were calculated using the equation of Yung-Chi et al., "Relationship Between the Inhibition Constant (Ki) and the Concentration of Inhibitor Which Causes 50 Percent Inhibition (ISO) of an Enzyme Reaction," *Biochemical Pharmacology* 22(23): 3099-3108 (1973), which is hereby incorporated by reference in its entirety, and dissociation constant values of [3H]-CP55940 and [3]-WIN55212-2 shown in Table 1.

TABLE 1

$K_i$ values were calculated by the Cheng & Prusoff equation (n = 3 or 4) using KD values of 0.8 nm for [3H]-CP55940 in membranes of CB2 cells and a Kd value of 2.1 nm for [3H]-WIN55212-2 in membranes of CB2 cells.

| Labelled cannabinoid | Unlabeled cannabinoid | CB2 $K_i$ (nM) |
| --- | --- | --- |
| [3H]-CP55940 | CP55940 | 1.8 ± 0.2 |
| | L759633 | 6.4 ± 2.2 |
| | L759656 | 11.8 ± 2.5 |
| | AM630 | 31.2 ± 12.4 |
| | SR144528 | 5.6 ± 1.1 |

TABLE 1-continued $K_i$ values were calculated by the Cheng & Prusoff equation (n = 3 or 4) using KD values of 0.8 nm for [3H]-CP55940 in membranes of CB2 cells and a Kd value of 2.1 nm for [3H]-WIN55212-2 in membranes of CB2 cells.

| Labelled cannabinoid | Unlabeled cannabinoid | CB2 $K_i$ (nM) |
| --- | --- | --- |
| [3H]-W1N55212-2 | AM630 | 37.5 ± 15.4 |
| | SR144528 | 4.1 ± 1.3 |

Generation and binding of the anti-CBD antibody. Reference CBD was extracted from the inflorescence of the Avidekel plant. 5% reference CBD was dissolved in caproic acid ($C_5H_{11}COOH$). 0.2 ml of this solution was injected with a 27-28 mm gauge needle into the lateral tail vein of BALB/Lac mice. The injections were repeated every other day for 14 days for a total of 7 injections. Each injection was followed by an in vivo electroporation of 80 pulses of 100 microseconds at 0.3 Hz with an electrical field magnitude of 2500 V/cm. Following cannabidiol immunization, mouse splenocytes were extracted and isolated. They were fused with myeloma cells by dielectrophoresis using a BTX ECM 2001 Electrofusion Generator, manufactured by BTX Harvard Apparatus, Holliston, Mass. USA. The fused cells were incubated in a hypoxanthine-aminopterin-thymidine medium (with respective concentrations 0.1 mM, 0.4 µM, and 0.016 mM) for between ten and fourteen days, resulting in the survival of only the B cell-myeloma hybrids. Following limiting dilution to one cell per plate, ELISA was used to select hybridomas that produced antibodies with higher binding to the pure CBD molecule. The antibody was linked to a Cytochrome P450 enzyme. Pentalenolactone was used as the Cytochrome P450 substrate. The hybridoma producing the antibody with the highest binding affinity, as measured by a molar weight increase in the Cannabidiol Antibody Complex (CAC), was cloned using supplemental media cultures containing interleukin-6.

Cloned hybridomas grew in culture medium RPMI-1640 with antibiotics and fetal bovine serum. A/G purification was used to extract monoclonal antibodies from hybridomas. The culture supernatant contained 46 micrograms/milliliter to 72 micrograms/milliliter of Cannabidiol monoclonal antibody (MCA). This antibody was maintained at −20° C. or lower until used. Fluorescence labelled ELISA was used to measure binding for each sample. The molar weight of the CAC was divided by the molar weight of the gold standard reference CAC to derive binding affinity values.

Ultracentrifugal CBD extraction. Plant tissue (from the inflorescence) was ultrasonically fractioned. The pulp and plasma were separated by centrifugation. The plasma fraction was further fractionated and studied by analytical ultra centrifuge to obtain the sedimentation coefficient of CBD. Isopycnic density gradient preparative ultracentrifugation (up to 130,000 RPM), using sodium bromide and cesium chloride, was then done to collect the purified CBD samples. This is not a commercially viable process but it provided enough mg of CBD to conduct the bioactivity test.

Solvent CBD extraction. For the solvent procedure, dried plant material was extracted at around 20° C. with ethanol, followed by methylene chloride, and separated uncarboxylated cannabinoids from carboxylated cannabinoids.

CBD isolation and analysis. Each fraction was identified by using the following methods: Silica gel eluting with $CHCl_3$; silica gel eluting with $C_6H_6$-MeOH—AcOH (88%: I 0%: 2%) (Mechoulam et al., "A New Tetrahydrocannabinolic Acid," *Tetrahedron Letters* 10(28):2339-2341 (1969); Korte et al., "Chemical Classification of Plants. XXVI.

Hashish Constituents by Thin-Layer Chromatography," *Journal of Chromatography* 13(1):90-98 (1964), which are hereby incorporated by reference in their entirety); Cannabinoid reference standards. Following CBD isolation and identification, Fast Blue B Salt colors were used for qualitative analysis. The cannabinoids were then analyzed after trimethyl-sililation, by GLC using OV225 (50' SCOT column) or OV17 (2% on Chromosorb W, 5' column). Acid cannabinoids were estimated after decarboxylation by heating in pyridine.

Fluorescence labelled ELISA was used to measure the bioactivity of sample.

Example 4

A Novel, Valid, Scalable CBD Bioactivity Test

Highly pure, naturally occurring CBD molecules were extracted from the Avidekel plant, obtained in 2014 from Tikun Olam, Israel, via sonic fractionation and ultra centrifugal separation. [$^3$H]-CP55940 displacement assays were performed for this reference sample using membrane fractions of CHO cells expressing recombinant human $CB_2$. Additionally, binding of an MCA, described herein, was tested for this reference sample. The resulting displacement and binding values were used as a reference standard against which 26 CBD samples (acquired from Natural Hemp Solutions, Atlanta Ga.) were compared.

A correlation between the CHO $CB_2$ binding and the MCA binding across 26 samples was investigated. If the MCA binding correlated to the CHO—$CB_2$, it could be used instead for quicker, more efficient testing.

Pearson correlation analysis was performed using R on the $CB_2$ and CAC binding values of the 26 CBD samples. The binding affinities to both the recombinant human $CB_2$ and the highest-affinity MCA are listed in Table 2 as a proportion relative to the binding affinity shown by a highly pure CBD molecule. Using the Pearson correlation analysis, it was found that these were highly correlated (Pearson coefficient=0.97). Thus, the bioactivity of CBD can be predicted using the MCA with high accuracy.

TABLE 2

Binding affinities for the MCA versus the CB2 complex in 26 CBD-producing plant samples. They were highly correlated (r = .97).

| Sample | MCA Affinity | CB2 Affinity |
|---|---|---|
| 1 | 0.78 | 0.81 |
| 2 | 0.34 | 0.42 |
| 3 | 0.25 | 0.29 |
| 4 | 0.32 | 0.3 |
| 5 | 0.34 | 0.36 |
| 6 | 0.31 | 0.33 |
| 7 | 0.24 | 0.25 |
| 8 | 0.29 | 0.34 |
| 9 | 0.32 | 0.3 |
| 10 | 0.29 | 0.31 |
| 11 | 0.25 | 0.25 |
| 12 | 0.31 | 0.32 |
| 13 | 0.35 | 0.33 |
| 14 | 0.31 | 0.31 |
| 15 | 0.25 | 0.26 |
| 16 | 0.3 | 0.31 |
| 17 | 0.27 | 0.24 |
| 18 | 0.25 | 0.24 |
| 19 | 0.32 | 0.29 |
| 20 | 0.21 | 0.24 |

TABLE 2-continued

Binding affinities for the MCA versus the CB2 complex in 26 CBD-producing plant samples. They were highly correlated (r = .97).

| Sample | MCA Affinity | CB2 Affinity |
|---|---|---|
| 21 | 0.26 | 0.24 |
| 22 | 0.44 | 0.41 |
| 23 | 0.33 | 0.41 |
| 24 | 0.81 | 0.8 |
| 25 | 0.3 | 0.22 |
| 26 | 0.19 | 0.22 |
| 27 | 0.78 | 0.81 |
| 28 | 0.34 | 0.42 |

A successful and scalable bioactivity test for CBD has been validated. Bioactivity values are expressed as a proportion between 0 and 1 as compared to the CHO—$CB_2$ binding of the purest CBD molecule able to be isolated. The lower the number, the lower the bioactivity. If a CBD molecule has a bioactivity below 0.5, one could expect to observe CBD—$CB_2$ binding at half the strength of a molecule with a bioactivity of 1. If a molecule had an observed bioactivity of 0.2, one could expect the binding affinity to be at ⅕ the strength of a molecule with a bioactivity of 1. This test will illuminate the distribution of bioactive molecules throughout various parts of the plant.

Example 5

Cannabis CBD Bioactivity by Plant Organ

It is well known, among growers, that the yield of CBD is variable across different organs in the cannabis plant, with the inflorescence producing the highest output (The tip of secreting hairs located mainly on female-plant contain resin glands that have a considerable amount of cannabinoids. These glands are fewer in number in the leaves (Zuardi, "Cannabidiol: From an Inactive Cannabinoid to a Drug with Wide Spectrum of Action," *Revista Brasileira de Psiquiatria* 30(3):271-280 (2008), which is hereby incorporated by reference in its entirety)). However, the bioactivity of CBD extracted from different organs has never been studied before.

Using the bioactivity test, validated in experiment 1, 4 regions from 48 different cultivars of cannabis obtained from the USA, India, China, and the Czech Republic were examined. Inflorescence, petioles, apical buds/leaves, and stalks were tested separately. A combination of sonic fractionation and ultra centrifugal separation was used on the inflorescence to obtain purified samples. Cold solvent extraction was also used to obtain CBD from the inflorescence, petioles, apical buds/leaves, and stalks.

A 1×5 ANOVA and appropriate post-hoc comparisons were conducted on bioactivity with plant organ as the only factor. Bioactivity means and standard errors were plotted.

Levene's test indicated heteroscedastic variances between the organs $F(4,235)=6.05, p<0.001$. As such, a robust ANOVA as described by Wilcox, Introduction to Robust Estimation & Hypothesis Testing. $3^{rd}$ edition. Elsevier, Amsterdam, The Netherlands. (2012), which is hereby incorporated by reference in its entirety, was conducted. It found a significant difference between the bioactivities of centrifuge-extracted inflorescence CBD (M=0.96, SD=0.02, solvent-extracted CBD from the inflorescence (M=0.86, SD=0.04), solvent-extracted CBD from the petioles (M=0.54, SD=0.03), solvent-extracted CBD from the apical buds/leaves (M=0.4, SD=0.04), and solvent-extracted CBD from the stalks (M=0.19, SD=0.02), $F(4, 70.38)=9885.21$, $p<0.001$. (20% trimmed means are presented above.)

Robust post-hoc comparisons (Mair et al., "Robust Statistical Methods in R Using the WRS2 Package," Technical Report, Harvard University (2016), which is hereby incorporated by reference in its entirety), revealed significant differences between each of the CBD source categories (See Table 3 for the psihat values of each comparison, and their associated confidence intervals).

TABLE 3

Psihat and corresponding confidence interval values (in brackets) for robust one-way ANOVA post-hoc comparisons of bioactivity. Psihat values for each post-hoc comparions were obtained using 20% trimmed means. Corresponding 95% confidence interval values are presented in brackets. All associated p-values were <.001.

|  | Influorescence | Petioles | Apical buds/Leaves | Stalks |
| --- | --- | --- | --- | --- |
| Influorescence Centrifuge | −.205 [−.222 to −.187] | −.769 [−.781 to −.756] | −.669 [−.685 to −.654] | −.344 [−.360 to −.329] |
| Influorescence |  | −.563 [−.583 to −.545] | −.464 [−.486 to −.443] | −.140 [−.161 to −.119] |
| Petioles |  |  | 0.99 [.082 to .117] | .424 [.407 to .441] |
| Apical buds/LeaveS |  |  |  | .325 [.306 to .344] |

Figure 4:
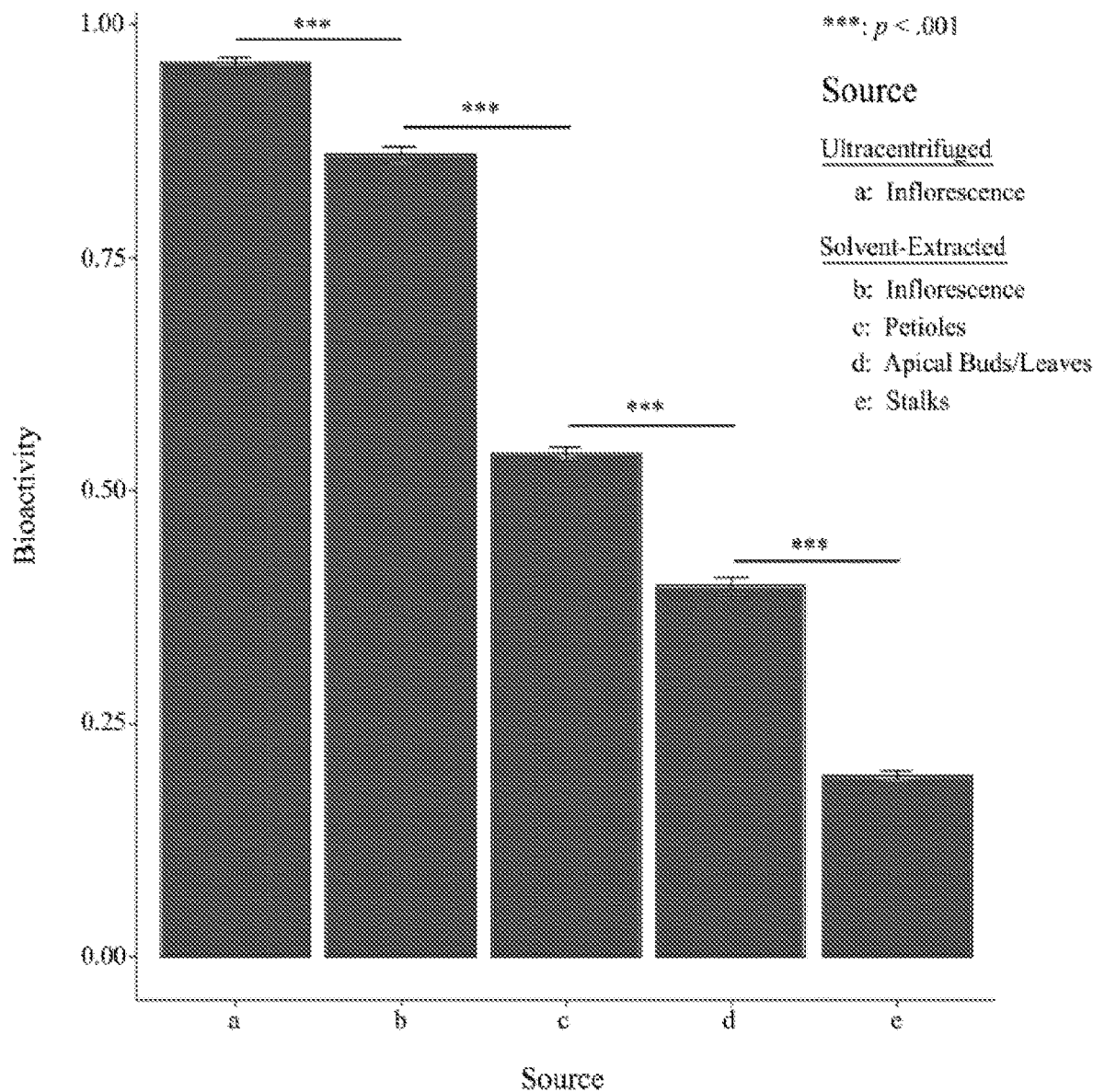
FIG. 4 shows the bioactivity of Cannabis sources. A highly canonical pattern emerged with influorescence producing the highest bioactivity. CBD source a was obtained through ultra centrifugal separation. CBD sources b, c, d, and e were obtained through cold-solvent extraction. Stan

In summary, the highest bioactivity CBD was found in the pods of each plant, with decreasing bioactivity in the petioles, apical buds/leaves, and stalks respectively (See FIG. 4). Individual bioactivity scores obtained per plant are provided in Table 4.

TABLE 4

48 cultivars of cannabis, and their associated bioactivity levels by plant organ.

| Cultivar | Ultra-centrifuged Inflorescence | Inflorescence | Petiole | Apical Bud/Leaf | Stalk |
| --- | --- | --- | --- | --- | --- |
| Uniko B | 0.956 | 0.902 | 0.517 | 0.36 | 0.169 |
| Kompolti | 0.98 | 0.881 | 0.538 | 0.383 | 0.192 |
| Fedora 17 | 0.976 | 0.865 | 0.52 | 0.43 | 0.191 |
| Fedora 17 | 0.919 | 0.892 | 0.509 | 0.468 | 0.194 |
| Fedora 17 | 0.95 | 0.907 | 0.569 | 0.409 | 0.201 |
| Ferimon 12 | 0.92 | 0.866 | 0.517 | 0.392 | 0.19 |
| Santhica 27 | 0.985 | 0.85 | 0.557 | 0.453 | 0.162 |
| Epsilon 68 | 0.991 | 0.859 | 0.575 | 0.37 | 0.171 |
| Futura 75 | 0.958 | 0.823 | 0.557 | 0.41 | 0.189 |
| Futura 75 | 0.963 | 0.85 | 0.53 | 0.443 | 0.176 |
| Felina 32 | 0.974 | 0.88 | 0.57 | 0.378 | 0.189 |
| Felina 34 | 0.946 | 0.817 | 0.588 | 0.392 | 0.183 |
| Juso 14 | 0.956 | 0.832 | 0.505 | 0.428 | 0.199 |
| Bialobrzeskie | 0.973 | 0.836 | 0.561 | 0.391 | 0.216 |
| Beniko | 0.984 | 0.844 | 0.516 | 0.434 | 0.175 |
| Chamaeleon | 0.969 | 0.85 | 0.525 | 0.384 | 0.17 |
| Chamaeleon | 0.972 | 0.907 | 0.513 | 0.397 | 0.226 |
| Carmagnola | 0.961 | 0.894 | 0.533 | 0.283 | 0.224 |
| Carmagnola | 0.973 | 0.862 | 0.565 | 0.431 | 0.21 |
| Carmagnola selezionata | 0.932 | 0.877 | 0.561 | 0.387 | 0.185 |
| Tiborszallasi | 0.94 | 0.882 | 0.531 | 0.359 | 0.192 |
| Fibranova | 0.974 | 0.893 | 0.51 | 0.408 | 0.23 |
| Delta-llosa | 0.949 | 0.852 | 0.54 | 0.397 | 0.228 |
| Delta-405 | 0.982 | 0.858 | 0.561 | 0.378 | 0.179 |
| Novgorod-Seversky, cv | 0.947 | 0.888 | 0.569 | 0.393 | 0.204 |
| Bernburgskaya Odnodomnaya, bm | 0.97 | 0.805 | 0.552 | 0.385 | 0.193 |
| Szegedi 9 | 0.936 | 0.88 | 0.521 | 0.373 | 0.166 |
| Fibrimulta 151 | 0.971 | 0.876 | 0.531 | 0.358 | 0.189 |
| Glukhovskaya 10 Zheltostebel'naya | 0.989 | 0.807 | 0.554 | 0.378 | 0.192 |
| Krasnodarsky 10 FB | 0.965 | 0.876 | 0.576 | 0.43 | 0.191 |
| Alpine Rocket | 0.951 | 0.841 | 0.62 | 0.427 | 0.198 |
| Alpine Rocket | 0.947 | 0.79 | 0.517 | 0.436 | 0.206 |
| Hindu Kush | 0.935 | 0.887 | 0.529 | 0.425 | 0.183 |
| Nortern Light | 0.993 | 0.871 | 0.546 | 0.36 | 0.221 |
| Snow White | 0.931 | 0.817 | 0.506 | 0.349 | 0.159 |
| Top 44 | 0.973 | 0.839 | 0.515 | 0.38 | 0.189 |
| Top 44 | 0.934 | 0.861 | 0.553 | 0.325 | 0.188 |
| F1 Fraise | 0.966 | 0.863 | 0.514 | 0.431 | 0.197 |
| B52 | 0.943 | 0.914 | 0.543 | 0.429 | 0.226 |
| Peace Maker | 0.946 | 0.848 | 0.534 | 0.346 | 0.197 |
| Big Bud | 0.951 | 0.9 | 0.536 | 0.379 | 0.2 |
| Big Skunk | 0.967 | 0.867 | 0.509 | 0.369 | 0.184 |
| F Fraise | 0.931 | 0.875 | 0.517 | 0.405 | 0.213 |
| Hawaii Maui Waui | 0.985 | 0.84 | 0.485 | 0.382 | 0.194 |
| Haze | 0.993 | 0.884 | 0.596 | 0.457 | 0.158 |
| Swaziland | 0.981 | 0.834 | 0.579 | 0.397 | 0.192 |
| Mexican Sativa | 0.963 | 0.825 | 0.528 | 0.451 | 0.207 |
| Ruderalis Indica | 0.942 | 0.789 | 0.499 | 0.398 | 0.186 |

These results showed a difference between extraction methodologies. The combination of sonic fractionation and ultra centrifugal separation produced CBD with the highest bioactivity. Sonic fractionation and ultra centrifugal extraction are labor- and equipment-intensive laboratory procedures, not fit for large-scale manufacture. By contrast, ethanol solvent extraction causes a small amount of degradation in bioactivity, but is scalable and relatively inexpensive to carry out. Ergo, it is a far more common procedure for commercial CBD production.

Among plant organs subjected to ethanol extraction, the results indicate a canonical pattern of CBD bioactivity. The inflorescence produced the highest bioactivity CBD molecules, with levels five times higher than CBD extracted from the stalk. Inflorescence should be used exclusively for the production of high bioactivity CBD. If commercial CBD suppliers have mixed in biomass from the stem and bark of the plant before extraction, it has lily led to low bioactivity in their products.

Example 6

Testing the Bioactivity of a Novel, Non-Cannabis, Plant Source of CBD

Using a plant from the Humulus family that produces CBD, a new plant was developed called Humulus Kriya. It does not produce THC, is from a family of plants considered GRAS (FDA Title 21, Volume 3, Sec 182.2-CAS 8060-28-4) and has been certified by FSSAI (Food Safety and Standards Authority of India) as a "Food Ingredient". It should not fall under the Scheduled List classification. The bioactivity profile of the various parts of H. Kriya was tested using the same methods as in Example 5.

The samples were made of six H. Kriya plants, provided by ImmunAG, LLP, India, and thirty one samples of ImmunAG oil extract.

Welch's t was used to compare CBD bioactivity of H. Kriya from all five groups to the cannabis samples. Individual bioactivity scores obtained per plant are provided in Table 5.

TABLE 5

6 samples of ImmunAG, and their associated bioactivity levels by plant organ.

| Cultivar | Ultra-centrifuged Inflorescence | Inflorescence | Petiole | Apical Bud/Leaf | Stalk |
| --- | --- | --- | --- | --- | --- |
| H. Kriya #3 | 0.964 | 0.829 | 0.536 | 0.465 | 0.212 |
| H. Kriya #5 | 0.947 | 0.798 | 0.532 | 0.414 | 0.195 |
| H. Kriya #6 | 0.956 | 0.883 | 0.549 | 0.399 | 0.215 |
| H. Kriya #11 | 0.961 | 0.96 | 0.551 | 0.445 | 0.188 |
| H. Kriya #14 | 0.941 | 0.835 | 0.519 | 0.402 | 0.21 |
| H. Kriya #17 | 0.932 | 0.851 | 0.536 | 0.355 | 0.182 |

Figure 5:
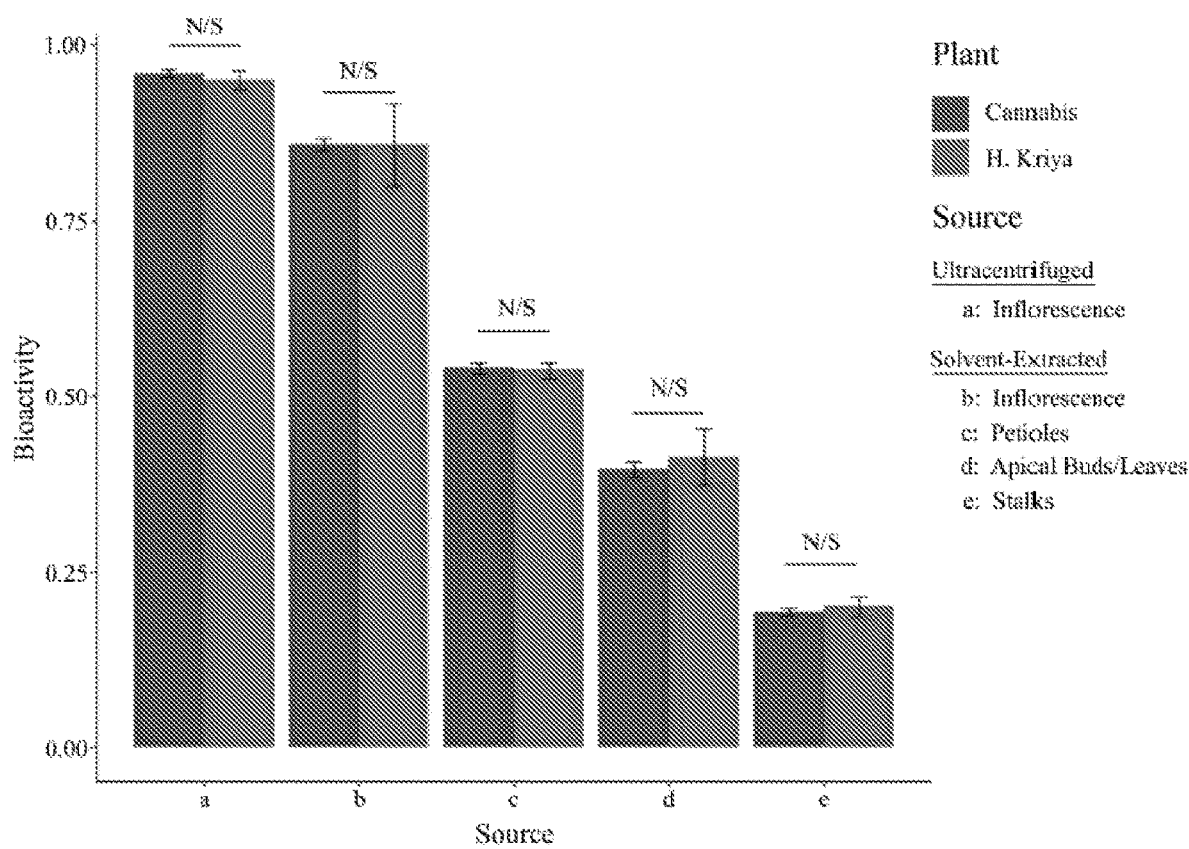
- FIG. 5 shows the bioactivity of H. Kriya and Cannabis sources. No significant differences were found between H. Kriya and cannabis for any of the organs.

The centrifuged pod CBD from H. Kriya (M=0.95, SD=0.01) showed no difference in bioactivity compared to cannabis samples, t(8.6594)=1.74,p=0.12. The solvent extracted pod CBD (M=0.86, SD=0.06) showed no difference, t(5.3803)=0.007,p=0.99. The solvent-extracted petiole CBD (M=0.54, SD=0.01) showed no difference, t(14.123)=0.373,p=0.715. The solvent-extracted leaf CBD (M=0.41, SD=0.04) showed no difference, t(6.164)=−1.0212, p=0.346. The solvent-extracted stem CBD (M=0.20, SD=0.01) showed no difference, t(7.322)=−1.143, p=0.289. It appears as though H. Kriya has an identical CBD bioactivity profile to the cannabis strains tested. Comparisons are shown in FIG. 5.

Identical CBD bioactivity was found between H. Kriya and Cannabis for CBD extracted from various parts of the plant. H. Kriya appears to be a viable cannabis alternative for CBD research. CBD from H. Kriya has no risk of THC contamination. It has been certified as a food ingredient by the Food Safety and Standards Authority of India.

Example 7

Examining the Bioactivity of Commercially Available CBD Products

The bioactivity of commercial CBD samples has never been examined. The results of commercial, cannabis-based, products were analyzed over the past 2 years. These samples were sent directly by vendors (Natural Hemp Solutions, Centuria Foods, BSPG, Isodiol, Hammer Enterprises, etc.) or sent by 3rd parties. The bioactivity results for individual vendors have not been published the bioactivity results for all of the vendors together has been anonymously presented.

There are many cannabimimetic molecules other than CBD. The two announced sources of CBD from non-hemp/cannabis sources are yeast and humulus. Samples of CBD could not be extracted from yeast. The bioactivity of CBD extracted from H. Kriya (ImmunAG) was tested and compared to commercial cannabis products.

Figure 6:
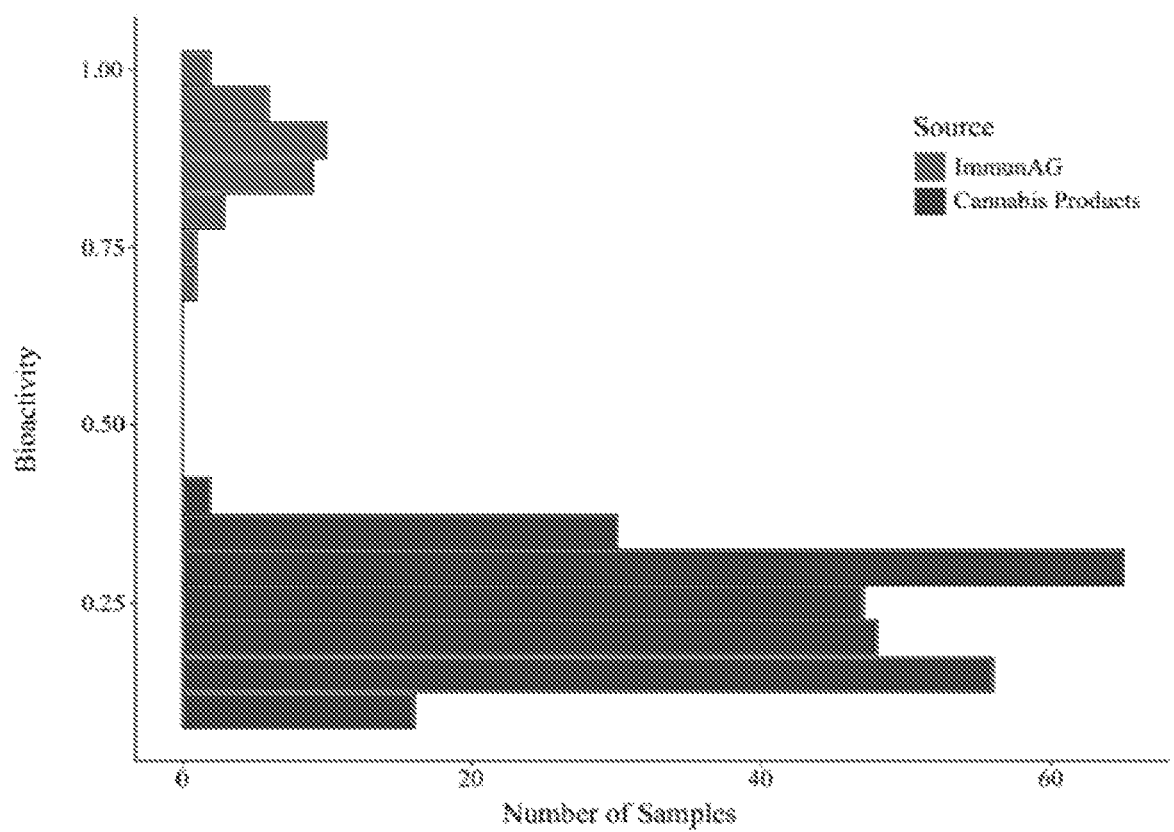
FIG. 6 shows comparisons of ImmunAG and Cannabis-based CBD products. H. Kriya-based ImmunAG shows higher bioactivity across all samples than cannabis-based commercial products.

The minimum bioactivity in commercial samples was 0.11 and the maximum was 0.41. The minimum bioactivity in ImmunAG was 0.72, and the maximum was 0.98. Bioactivity scores for both classes of product are shown in FIG. 6.

When comparing the CBD bioactivity in ImmunAG (M=0.88, SD=0.06) to products on the market (M=0.23, SD=0.07), Welch's t found a significant difference in bioactivity, t(41.288)=53.41,p<1.001.

Commercial CBD bioactivity were low, having values consistent with the lower bioactive organs—stalks, stems, barks and leaves. It is possible that suppliers have been using biomass rich in stalk, stem and leaves to comply with regulations and increase mass. The caution is that low bioactive CBD may not produce desirably intense immunologic cell signals.

Commercial CBD bioactivity was also quite variable, with a minimum of 0.11 and a maximum of 0.41. The highest commercial sample had almost four times the potency of the lowest sample. Left unchecked, low bioactivity CBD are likely to confound medical use or research and produce spurious results.

ImmunAG samples ranged from 0.72 to 0.98, with the lowest ImmunAG bioactivity higher than the highest commercial cannabis-based CBD bioactivity. This is not surprising because ImmunAG is only made from the inflorescence of H. Kriya. An audit revealed that carefully regulated processing conditions also enabled ImmunAG to maintain significantly high bioactivity.

Discussion of Examples 4-7

It was found that use of mono clonal antibody testing of CBD bioactivity was viable. It was found that CBD extracted from different plant organs had different bioactivity, with inflorescence having the highest bioactivity, and stalks/stems having the lowest. A non cannabis CBD-producing plant, H. Kriya, that has a bioactivity profile similar to cannabis, was evaluated. It was found that hemp/cannabis based CBD products sold commercially have low bioactivity. It was found that commercial CBD products made from it H. Kriya had the highest bioactivity.

CBD-CB2 interactions are responsible for a wide range of immunologic effects. The samples studied had widely varying levels of bioactivity. It is likely that bioactivity levels have been silently confounding historical research results. Scientific studies utilizing CBD for medical research should strive to use products with the highest bioactivity levels.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated antibody or antigen binding fragment thereof, wherein said isolated antibody or antigen binding fragment thereof binds to cannabidiol, said cannabidiol having the structure of Formula I

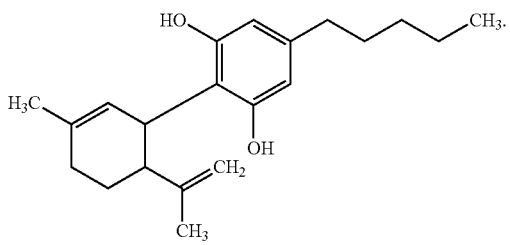

Formula I and wherein said isolated antibody or antigen binding fragment thereof comprises
a $V_H$ comprising the H-CDR1 of SEQ ID NO: 1, the H-CDR2 of SEQ ID NO: 2, and the H-CDR3 of SEQ ID NO:3, and
a $V_L$ comprising the L-CDR1 of SEQ ID NO: 4, the L-CDR2 of SEQ ID NO: 5, and the L-CDR3 of SEQ ID NO:6.

2. The isolated antibody or antigen binding fragment thereof of claim 1, wherein said isolated antibody or antigen binding fragment thereof binds the delta-2 isomer of Formula I (2-(6-isopropenyl-3-methyl-2-cyclohexen-1-yl)-5-pentyl-1,3-benzenediol).

3. The isolated antibody or antigen binding fragment thereof of claim 1, wherein said isolated antibody is an IgG antibody.

4. The isolated antibody or antigen binding fragment thereof of claim 1, wherein said antigen binding fragment thereof is a Fab fragment.

5. The isolated antibody or antigen binding fragment thereof of claim 1, wherein said isolated antibody comprises a single-chain antibody.

6. The isolated antibody or antigen binding fragment thereof of claim 1, wherein said isolated antibody or binding fragment thereof comprises a heavy chain variable region ($V_H$) comprising an amino acid sequence that is at least 90% identical to the amino acid sequence of SEQ ID NO: 7.

7. The isolated antibody or antigen binding fragment thereof of claim 6, wherein said $V_H$ comprises the amino acid sequence of SEQ ID NO: 7.

8. The isolated antibody or antigen binding fragment thereof of claim 1, wherein said isolated antibody or binding fragment thereof comprises a light chain variable region ($V_L$) comprising an amino acid sequence that is at least 90% identical to the amino acid sequence of SEQ ID NO: 8.

9. The isolated antibody or antigen binding fragment thereof of claim 8, wherein said ($V_L$) comprises the amino acid sequence of SEQ ID NO: 8.

10. The isolated antibody or antigen binding fragment thereof of claim 1, wherein said isolated antibody comprises a $V_H$ having the amino acid sequence of SEQ ID NO: 7 and a $V_L$ having the amino acid sequence of SEQ ID NO: 8.

11. A hybridoma producing the isolated antibody of claim 1.

12. An isolated polynucleotide encoding the isolated antibody or antigen binding fragment thereof of claim 1.

13. A vector comprising the isolated polynucleotide of claim 12.

14. A host cell comprising the vector of claim 13.

15. A method of detecting cannabidiol in a sample, said method comprising:
   contacting the sample with the isolated antibody or antigen binding fragment thereof of claim 1 and
   detecting the isolated antibody or antigen binding fragment thereof bound to said cannabidiol if present in the sample.

16. A method of determining the bioactivity of cannabidiol, said method comprising:
   providing a sample containing a known amount of cannabidiol;
   contacting the sample with the isolated antibody or antigen binding fragment thereof of claim 1;
   detecting the isolated antibody or antigen binding fragment thereof bound to said cannabidiol in the sample;
   measuring the amount of the isolated antibody or antigen binding fragment thereof bound to said cannabidiol; and
   determining the bioactivity of the cannabidiol in the sample based on said measuring.

17. A kit comprising:
   the isolated antibody or antigen binding fragment thereof of claim 1.

* * * * *